US010299934B2

(12) United States Patent
Seifert et al.

(10) Patent No.: US 10,299,934 B2
(45) Date of Patent: May 28, 2019

(54) EXPANDABLE VERTEBRAL IMPLANT

(71) Applicant: Globus Medical, Inc., Audubon, PA (US)

(72) Inventors: Jody L. Seifert, Birdsboro, PA (US); Chad Glerum, Pennsburg, PA (US); Mark Weiman, Coatesville, PA (US); Mark Adams, Coatesville, PA (US); David C. Paul, Phoenixville, PA (US)

(73) Assignee: GLOBUS MEDICAL, INC, Audubon, PA (US)

( * ) Notice: Subject to any disclaimer, the term of this patent is extended or adjusted under 35 U.S.C. 154(b) by 168 days.

(21) Appl. No.: 13/837,452

(22) Filed: Mar. 15, 2013

(65) Prior Publication Data

US 2014/0163683 A1 Jun. 12, 2014

Related U.S. Application Data

(63) Continuation-in-part of application No. 13/711,204, filed on Dec. 11, 2012, now abandoned.

(51) Int. Cl.
*A61F 2/44* (2006.01)
*A61F 2/28* (2006.01)
(Continued)

(52) U.S. Cl.
CPC .......... *A61F 2/4455* (2013.01); *A61F 2/4425* (2013.01); *A61B 17/8042* (2013.01);
(Continued)

(58) Field of Classification Search
CPC .......... A61F 2/4455; A61F 2/44; A61F 2/447; A61F 2/442; A61F 2002/30518;
(Continued)

(56) References Cited

U.S. PATENT DOCUMENTS 4,349,921 A 9/1982 Kuntz
4,599,086 A 7/1986 Doty
(Continued)

FOREIGN PATENT DOCUMENTS

DE 4012622 C1 7/1991
DE 4327054 C1 4/1995
(Continued)

*Primary Examiner* — Eric S Gibson
*Assistant Examiner* — Marcela I Shirsat

(57) ABSTRACT

A joint spacer therapeutically maintains separation of bones of a joint. A carriage is slideably retained within the frame and has at least one ramped surface. An actuator screw is threadably engaged with the frame, and rotatably connected to the carriage, to cause the carriage to slideably move within the frame when the actuator screw is rotated. First and second endplates engage the bones of the joint, and each has at least one ramped surface that is mateable with the ramped surface of the carriage, whereby when the carriage is slideably moved by rotation of the actuator screw, the endplates ramped surface slides against the carriage ramped surface to cause the endplates to move along an axis transverse to the longitudinal axis of the frame, to increase the height of the spacer. Piercing elements are connected to the carriage to pierce bone of the joint when the carriage is moved.

20 Claims, 17 Drawing Sheets

(51) Int. Cl.
   *A61F 2/30* (2006.01)
   *A61F 2/46* (2006.01)
   *A61B 17/80* (2006.01)

(52) U.S. Cl.
   CPC . *A61F 2002/2835* (2013.01); *A61F 2002/305* (2013.01); *A61F 2002/30387* (2013.01); *A61F 2002/30433* (2013.01); *A61F 2002/30471* (2013.01); *A61F 2002/30507* (2013.01); *A61F 2002/30523* (2013.01); *A61F 2002/30556* (2013.01); *A61F 2002/30578* (2013.01); *A61F 2002/30579* (2013.01); *A61F 2002/30904* (2013.01); *A61F 2002/4635* (2013.01)

(58) Field of Classification Search
   CPC .... A61F 2002/2835; A61F 2002/30523; A61F 2002/443; A61F 2002/30579; A61F 2002/30578; A61F 2002/30904; A61F 2002/30433; A61F 2002/30537; A61F 2002/30556
   USPC .......................................... 623/17.11–17.16
   See application file for complete search history.

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochshuler et al. |
| 6,080,193 A | 6/2000 | Hochshuler et al. |
| 6,099,531 A | 8/2000 | Bonutti |
| 6,113,637 A * | 9/2000 | Gill ....................... A61F 2/4425 623/17.15 |
| 6,126,689 A | 10/2000 | Brett |
| 6,176,882 B1 | 1/2001 | Biedermann et al. |
| 6,214,050 B1 * | 4/2001 | Huene ....................... 623/17.15 |
| 6,258,125 B1 | 7/2001 | Paul et al. |
| 6,436,140 B1 | 8/2002 | Liu |
| 6,558,423 B1 | 5/2003 | Michelson |
| 6,562,074 B2 | 5/2003 | Gerbec et al. |
| 6,576,016 B1 | 6/2003 | Hochshuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,773,460 B2 | 8/2004 | Jackson |
| RE38,614 E | 10/2004 | Paul |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,220,280 B2 | 5/2007 | Kast |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,727,280 B2 | 6/2010 | McLuen |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,058 B2 | 9/2010 | Froehlich |
| 7,799,081 B2 | 9/2010 | McKinley |
| 7,815,683 B2 | 10/2010 | Melkent et al. |
| 7,828,849 B2 | 11/2010 | Lim |
| 7,837,734 B2 | 11/2010 | Zucherman et al. |
| 7,850,733 B2 | 12/2010 | Baynham |
| 7,875,078 B2 | 1/2011 | Wysocki et al. |
| 7,883,543 B2 | 2/2011 | Sweeney |
| 7,901,409 B2 | 3/2011 | Canaveral et al. |
| 7,909,869 B2 | 3/2011 | Gordon |
| 7,951,199 B2 | 5/2011 | Miller |
| 7,976,867 B2 | 6/2011 | Barreiro |
| 8,062,375 B2 | 11/2011 | Glerum |
| 8,105,382 B2 | 1/2012 | Olmos |
| 8,123,810 B2 | 2/2012 | Gordon |
| 8,128,701 B2 | 3/2012 | Kast |
| 8,137,405 B2 | 3/2012 | Kostuik et al. |
| 8,187,332 B2 | 5/2012 | McLuen |
| 8,267,939 B2 | 9/2012 | Cipoletti |
| 8,273,129 B2 | 9/2012 | Baynham |
| 8,382,842 B2 | 2/2013 | Greenhalgh |
| 8,398,713 B2 | 3/2013 | Weiman |
| 8,647,386 B2 | 2/2014 | Gordon |
| 2002/0045945 A1 | 4/2002 | Liu |
| 2002/0068976 A1 | 6/2002 | Jackson |
| 2002/0068977 A1 | 6/2002 | Jackson |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte |
| 2005/0113916 A1 | 5/2005 | Branch, Jr. |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270961 A1 * | 11/2007 | Ferguson ................... 623/17.11 |
| 2007/0270963 A1 | 11/2007 | Melkent et al. |
| 2007/0270968 A1 * | 11/2007 | Baynham ................ A61F 2/447 623/17.11 |

(56) References Cited

U.S. PATENT DOCUMENTS

| | | |
|---|---|---|
| 2007/0282448 A1* | 12/2007 | Abdou .................. A61F 2/441 623/17.15 |
| 2008/0021559 A1 | 1/2008 | Thramann |
| 2008/0065222 A1 | 3/2008 | Hamada |
| 2008/0114467 A1 | 5/2008 | Capote |
| 2008/0140207 A1 | 6/2008 | Olmos et al. |
| 2008/0147194 A1 | 6/2008 | Grotz |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Amicus |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac |
| 2008/0319487 A1 | 12/2008 | Fielding et al. |
| 2008/0319549 A1 | 12/2008 | Greenhalgh et al. |
| 2009/0024217 A1 | 1/2009 | Levy |
| 2009/0076616 A1 | 3/2009 | Duggal |
| 2009/0125062 A1 | 5/2009 | Uri |
| 2009/0149956 A1 | 6/2009 | Greenhalgh et al. |
| 2009/0149959 A1 | 6/2009 | Conner et al. |
| 2009/0192616 A1* | 7/2009 | Zielinski .................. 623/17.16 |
| 2009/0204218 A1 | 8/2009 | Richelsoph |
| 2009/0210062 A1* | 8/2009 | Thalgott .............. A61F 2/4465 623/17.16 |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza |
| 2009/0292361 A1 | 11/2009 | Lopez |
| 2009/0299478 A1 | 12/2009 | Carls et al. |
| 2009/0312763 A1 | 12/2009 | Mccormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1 | 4/2011 | Glerum |
| 2011/0144755 A1 | 6/2011 | Baynham |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0226357 A1 | 9/2012 | Varela |
| 2012/0265309 A1* | 10/2012 | Glerum .................. A61F 2/447 623/17.16 |
| 2012/0277870 A1 | 11/2012 | Wolters et al. |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158669 A1 | 6/2013 | Sungarian |

FOREIGN PATENT DOCUMENTS

| | | |
|---|---|---|
| EP | 0576379 B1 | 6/1993 |
| EP | 0610837 B1 | 7/1994 |
| FR | 2794968 | 12/2000 |
| JP | 2000-513263 | 10/2000 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |

* cited by examiner

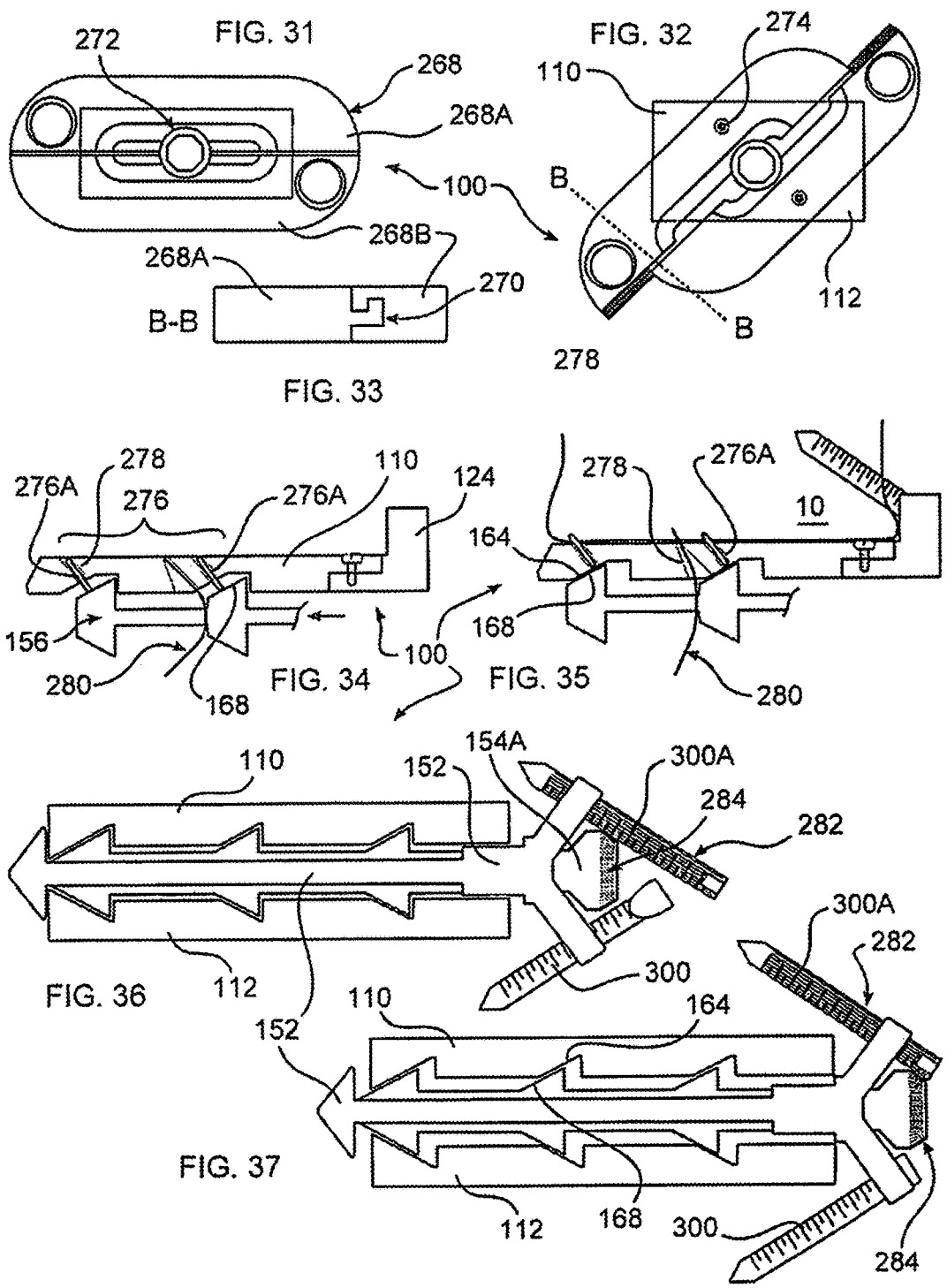

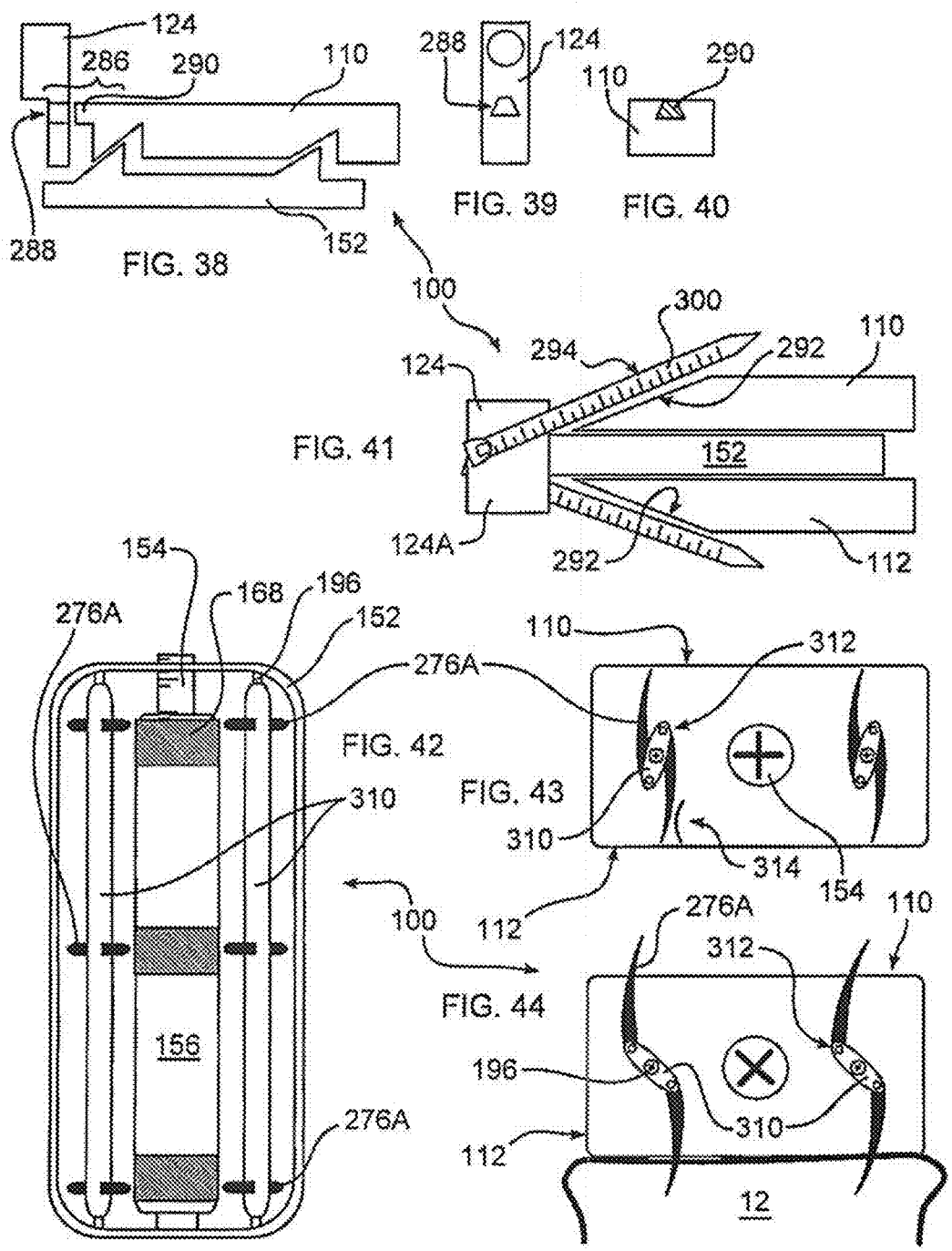

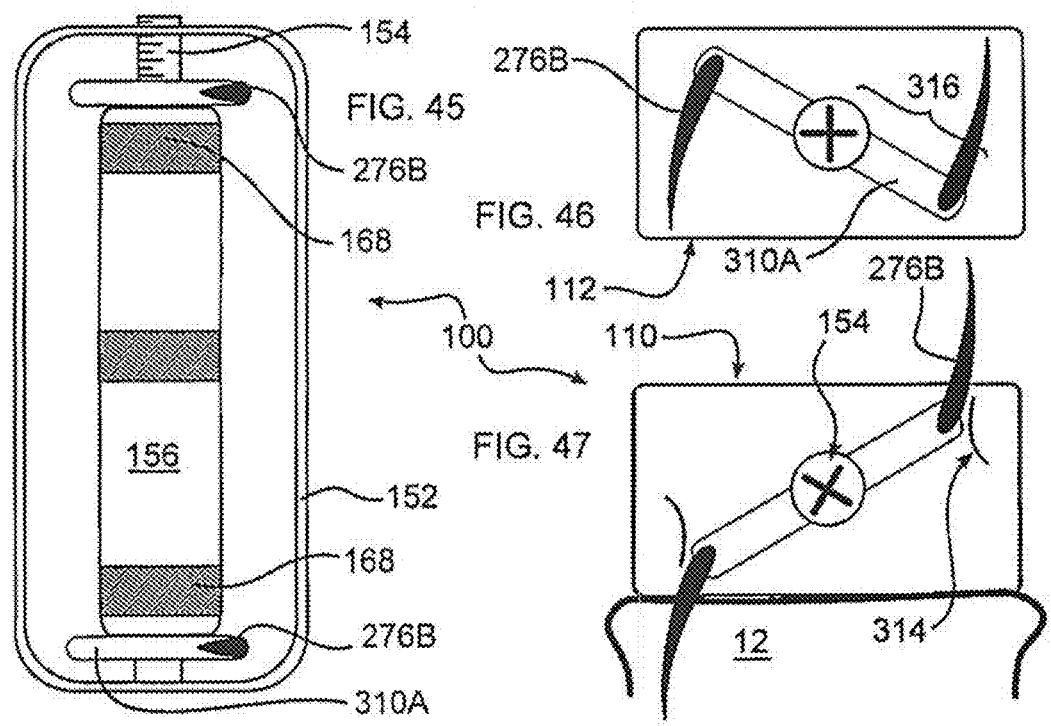
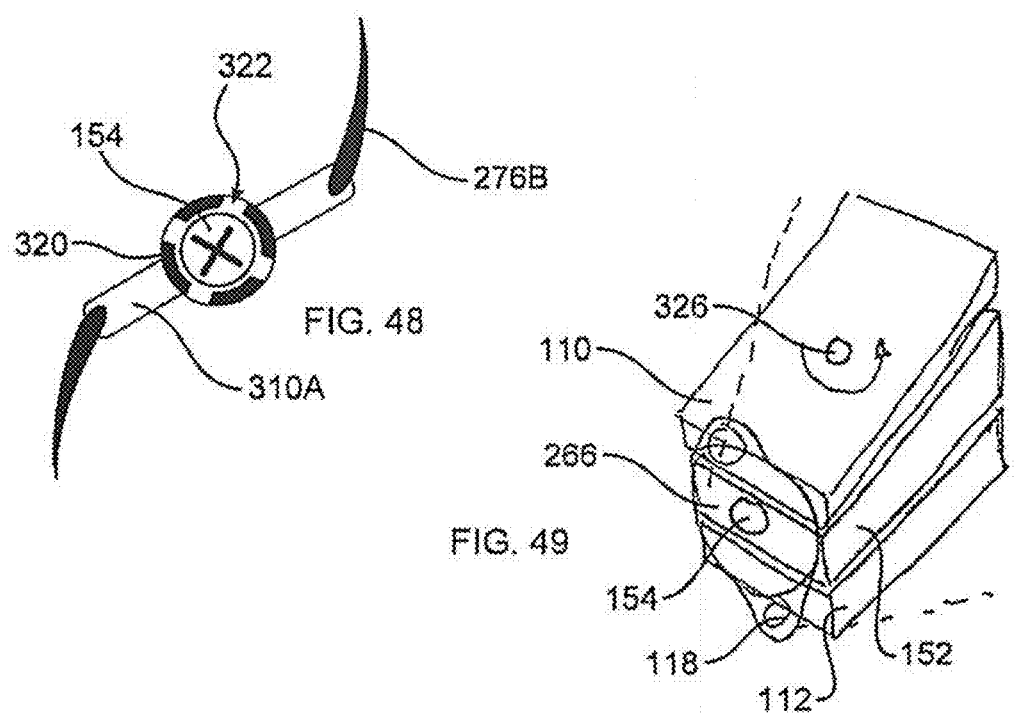

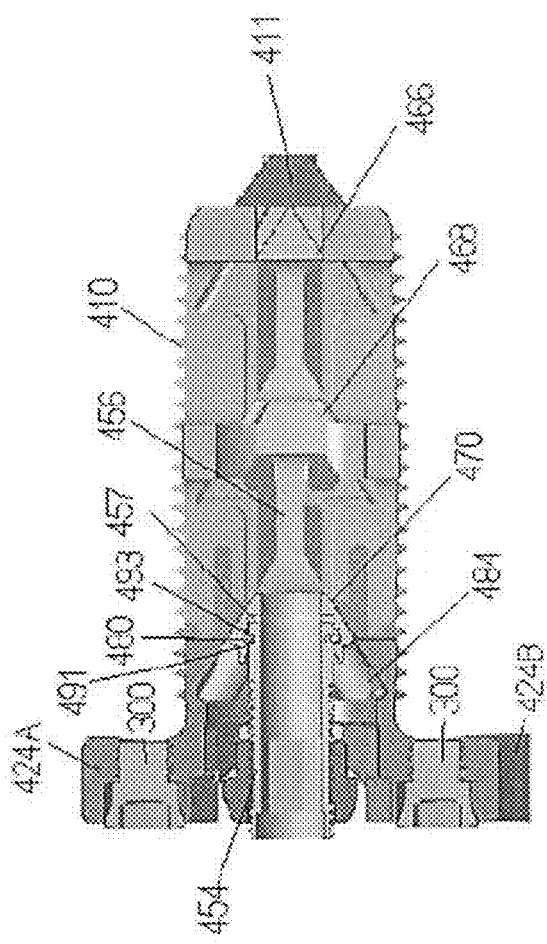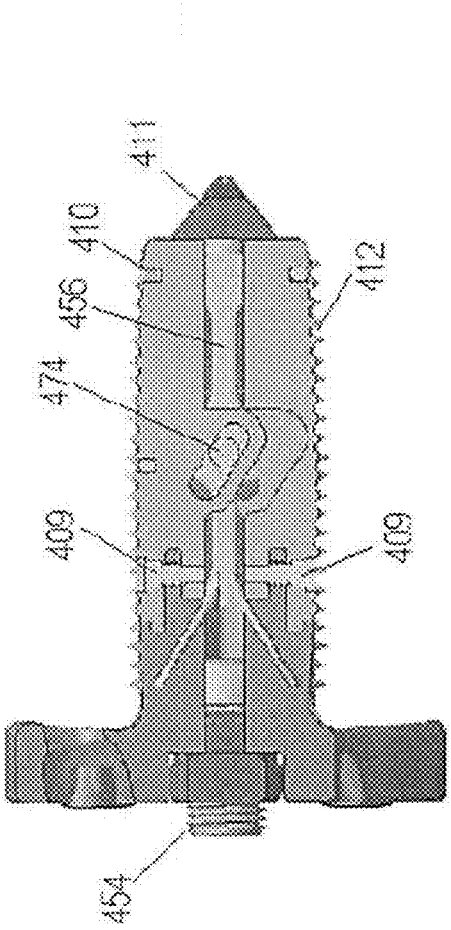

EXPANDABLE VERTEBRAL IMPLANT

CROSS REFERENCE TO RELATED APPLICATIONS

This patent application is a continuation-in-part application of U.S. patent application Ser. No. 13/711,204, filed on Dec. 11, 2012, the entire contents of which are incorporated by reference.

FIELD OF THE INVENTION

This invention relates to stabilizing adjacent vertebrae of the spine by inserting an intervertebral spacer, and more particularly, an intervertebral spacer that is adjustable in height with plates for fixation.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY OF THE INVENTION

In accordance with the disclosure, a joint spacer for therapeutically maintaining a separation of bones of a joint, comprises a frame having distal and proximal ends defining a longitudinal axis extending therebetween; a carriage slideably retained within the frame and having at least one ramped surface, the carriage further including a threaded portion; an actuator screw threadably engaged with the frame, the actuator screw configured to bear against the carriage to cause the carriage to slideably move within the frame when the actuator screw is rotated; a first endplate configured to engage a first bone of the joint, and having at least one surface mateable with the at least one carriage ramped or a feature surface, whereby when the carriage is slideably moveable by rotation of the actuator screw, the at least one endplate ramped surface slides against the at least one carriage ramped surface to cause the first endplate to move along an axis transverse to the longitudinal axis to increase a height of the spacer; and a second endplate configured to engage a second bone of the joint.

In one embodiment thereof, the carriage includes at least two ramped surfaces, and the second endplate includes at least one ramped surface mateable with at least one of the at least two ramped surfaces of the carriage, whereby when the carriage is slideably moved by rotation of the actuator screw, the at least one second endplate ramped surface slides against the at least one additional carriage ramped surface to cause the second endplate to move along an axis transverse to the longitudinal axis to increase a height of the spacer.

In other embodiments thereof, the first endplate is configured to abut the frame as the first endplate is moved along an axis transverse to the longitudinal axis, whereby the first endplate moves substantially only along an axis transverse to the longitudinal axis; the first endplate includes at least one aperture through which a fastener may pass to secure the first endplate to a bone of the joint; the spacer further includes a blocking mechanism to prevent backing out of a fastener passed through the first endplate; and the first endplate includes one or more projections configured to engage bone of the joint when the implant is positioned between bones of the joint.

In further embodiments thereof, at least one of the first and second endplates is composed of two interconnected portions of dissimilar materials; one of the dissimilar materials is metallic and includes at least one aperture through which a fastener may be passed to attach the implant to a bone of the joint; and one dissimilar material is polymeric, and another dissimilar material is metallic. Other possible materials include carbon fiber, bone, etc.

In yet further embodiments thereof, the actuator screw includes a flange (or a pocket or other feature), and the carriage includes a flange (or c-clip or other feature) rotatably mateable with the actuator screw flange; the spacer further includes a thrust washer interposed between the actuator screw and the carriage; the spacer further includes a polymeric material configured to press against the actuator screw to reduce a potential for unintended rotation of the actuator screw; and the spacer further includes a plate having at least one aperture sized and dimensioned to receive an elongated fastener for fastening the spacer to bone of the joint, the plate being releaseably detachable from the spacer to reduce an profile of the spacer during insertion of the spacer into the body, the plate attached to the spacer inside the body.

In other embodiments thereof, the plate and the frame include mating portions of a twist-lock connector operable to connect the plate to the frame when the spacer is inside the body; the plate and the frame include mating portions of a snap-fit interference connector operable to connect the plate to the frame when the spacer is inside the body or outside; the plate includes hinged portions, the hinged portions foldable to reduce a profile of the plate during insertion of the plate into the body; the at least one surface mateable with the at least one carriage ramped surface is at least one ramp; the at least one carriage ramp is disposed upon at least one cam, the cam rotatable to bear the at least one carriage ramp against the at least one surface of the first endplate; the first endplate includes a rotatable portion having first and second transverse axes of different lengths; and the rotatable portion is passable through an interior of the spacer.

In other embodiments thereof, the first endplate includes an aperture sized and dimensioned to receive an elongated fastener operable to pass through the aperture to affix the spacer to bone of the joint, the aperture movable with the first endplate as the first endplate is moved along the axis transverse to the longitudinal axis; and the first endplate includes a first portion having at least one aperture through which a fastener may pass to secure the first endplate to a bone of the joint, and a second portion configured to support bone of the joint, the first and second portions mutually connected by a dovetail or other type of connection.

In additional embodiments thereof, the spacer further includes a rotatable plate having at least two apertures through each of which a fastener may pass to secure the spacer to a bone of the joint, the rotatable plate rotatable after the spacer has been implanted within the body, to overlie the at least two apertures with bone of the joint; the spacer further includes a rotatable plate having at least two apertures through each of which a fastener may pass to secure the spacer to a bone of the joint, the rotatable plate rotatable after the spacer has been implanted within the body, to overlie the at least two apertures with bone of the joint; the spacer further includes at least one rotatable plate having an aperture through which a fastener may pass to secure the spacer to a bone of the joint, the rotatable plate rotatable after the spacer has been implanted within the body, to overlie the aperture with bone of the joint; and the spacer further includes at least two plates rotatably connectable to the spacer, each plate slidably connected to the other by a dovetail joint, each plate having at least one aperture through which a fastener may pass to secure the spacer to bone of the joint, the plates rotatable after the spacer has been implanted within the body, and each of the at least two plates slideable with respect to the other, to overlie the aperture of each plate with bone of the joint.

In yet further embodiments thereof, at least one of the carriage ramped surfaces is operative to push a piercing element through an aperture in the first endplate, the piercing element operative to pierce bone of the joint to secure the spacer within the body; the spacer further includes a bone screw having bone engaging threads and gear teeth, and the actuator screw including gear teeth engageable with the gear teeth of the bone screw, the actuator screw thereby rotated when the bone screw is threaded into bone of the joint; the spacer further includes a plate having an aperture through which a fastener may be passed to connect the spacer to bone of the joint, the plate including a dovetail portion; and the first endplate including a dovetail portion mateable with the dovetail portion of the plate, the plate and the first endplate thereby securely connectable to each other; and the spacer further includes a channel formed within the first endplate, the channel sized and dimensioned to receive an elongate portion of a fastener operative to secure the spacer within the body.

In other embodiments thereof, the spacer further includes at least one elongate rotatable deployer pivotally connected to the frame; at least one piercing element connected to the deployer, the at least one piercing element operable to pierce bone of the joint when the rotatable deployer is rotated within the body; the at least one piercing element is pivotally connected to the deployer to thereby enter bone of the body at a desired angle relative to a plane of the first endplate; the at least one rotatable deployer rotates about a common axis with respect to the actuator screw; the at least one rotatable deployer rotates when the actuator screw is rotated; and the at least one rotatable deployer rotates independently of the actuator screw.

In yet further embodiments thereof, the first endplate is pivotally connected to the frame; the first endplate pivots about the pivotal connection, about an axis extending transverse to the longitudinal axis; and the first endplate is connected to the frame to allow roll, pitch, and yaw movement of the first endplate with respect to the frame.

In another embodiment of the disclosure, a joint spacer for therapeutically maintaining a separation of bones of a joint, comprises a frame having distal and proximal ends defining a longitudinal axis extending therebetween; a carriage slideably retained within the frame and having at least one ramped surface, the carriage further including a flange; an actuator screw threadably engaged with the frame, the actuator screw including a flange rotatably mateable with the carriage flange, whereby the carriage is slideably moved when the actuator screw is rotated; a first endplate configured to engage a first bone of the joint, and having at least one ramped surface mateable with the at least one carriage ramped surface, whereby when the carriage is slideably moved by rotation of the actuator screw in a first direction, the at least one endplate ramped surface slides against the at least one carriage ramped surface to cause the first endplate to move along an axis transverse to the longitudinal axis to increase a height of the spacer; and a second endplate configured to engage a second bone of the joint.

In various embodiments thereof, when the actuator screw is rotated in an opposite, second direction, the at least one endplate ramped surface is slideable against the at least one carriage ramped surface to cause the first endplate to move along an axis transverse to the longitudinal axis to decrease a height of the spacer; the first endplate includes a metallic portion having an aperture through which a fastener may be passed for connecting the implant to body tissue, the first endplate further having a polymeric portion connected to the metallic portion, the polymeric portion sized and dimensioned to support a bone of the joint; the frame and the first endplate include mateable dovetailed portions configured to maintain an orientation of the first endplate and the frame when the first endplate is positioned proximate the frame.

In another embodiment of the disclosure, a method for therapeutically maintaining a separation of bones of a joint, comprises inserting a spacer between bones of the joint, the spacer including—a frame having distal and proximal ends defining a longitudinal axis extending therebetween; a carriage slideably retained within the frame and having at least one ramped surface, the carriage further including a flange; an actuator screw threadably engaged with the frame, the actuator screw including a flange rotatably mateable with the carriage flange, whereby the carriage is slideably moved when the actuator screw is rotated; a first endplate configured to engage a first bone of the joint, and having at least one ramped surface mateable with the at least one carriage ramped surface, whereby when the carriage is slideably moved by rotation of the actuator screw in a first direction, the at least one endplate ramped surface slides against the at least one carriage ramped surface to cause the first endplate to move along an axis transverse to the longitudinal axis to increase a height of the spacer; and a second endplate configured to engage a second bone of the joint; the spacer inserted when the first endplate is positioned proximate the frame; and slideably moving, by rotation of the actuator screw, the at least one endplate ramped surface against the at least one carriage ramped surface to cause the first endplate to move along an axis transverse to the longitudinal axis to increase a height of the spacer to maintain a separation of bones of the joint.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which:

FIG. 31 depicts an embodiment of a spacer of the disclosure including two rotatable fixation portions connected by a sliding dovetail connection;

FIG. 32 depicts the spacer of FIG. 31, the fixation portions relatively displaced and rotated;

FIG. 33 depicts a cross-section the spacer of FIG. 31;

FIG. 34 depicts an embodiment of a spacer of the disclosure, including deployable piercing elements;

FIG. 35 depicts the spacer of FIG. 34, the piercing elements deployed;

FIG. 36 depicts an embodiment of a spacer of the disclosure, including a bone fixation device having gear teeth mateable with gear teeth of an endplate actuator screw;

FIG. 37 depicts the spacer of FIG. 36, the bone fixation device deployed to engage bone, and to increase a height of the spacer;

FIG. 38 depicts an embodiment of a spacer of the disclosure, including a dovetail connection between a fixation portion, and a bone endplate support portion;

FIG. 39 depicts the fixation portion of the spacer of FIG. 38;

FIG. 40 depicts the bone endplate support portion of the spacer of FIG. 38;

FIG. 41 depicts an embodiment of a spacer in accordance with the disclosure, including channels in endplate portions;

FIG. 42 depicts a top view of an embodiment of a spacer in accordance with the disclosure having deployment arms rotatably supporting piercing elements;

FIG. 43 depicts a cross section of the spacer of FIG. 42;

FIG. 44 depicts the spacer of FIG. 43, the piercing elements deployed;

FIG. 45 depicts an embodiment of a spacer in accordance with the disclosure, including a deployment arm having a common axis with an actuator screw;

FIG. 46 depicts a cross section of the spacer of FIG. 45;

FIG. 47 depicts the spacer of FIG. 46, the piercing elements deployed;

FIG. 48 illustrates an alternative spacer in accordance with FIG. 45, the deployment arm independently rotatable; and FIG. 49 illustrates an embodiment of a spacer in accordance with the disclosure, an endplate pivotable about a transverse axis.

FIG. 52 illustrates a side cross-sectional view of the alternative spacer of FIG. 50.

FIG. 53 illustrates a different cross-sectional view of the alternative spacer of FIG. 50.

DETAILED DESCRIPTION OF THE INVENTION

Figure 1:
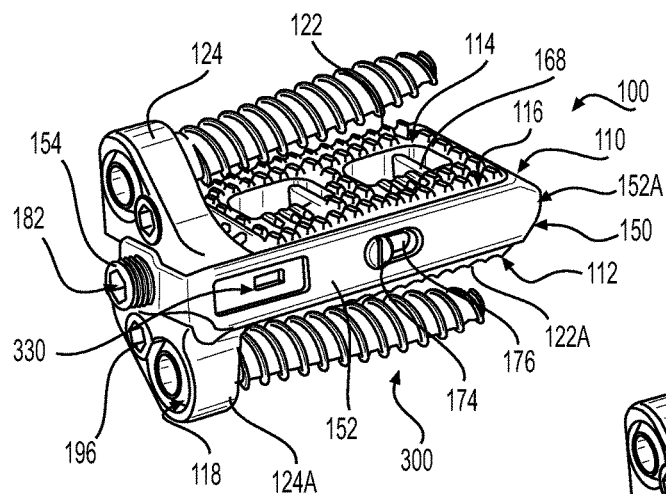
FIG. 1 depicts a perspective view of a spacer in accordance with the disclosure, including bone fasteners, the spacer in a reduced height, or compressed configuration.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

With reference to FIGS. 1-7, spacer 100 is operative, when positioned between adjacent bones of a joint, such as for example vertebrae 10, 12 (shown in FIG. 7), to stabilize a joint formed between adjacent vertebrae. Spacer 100 has a collapsed state or height, illustrated in FIGS. 1 and 3, and an expanded state or height, illustrated in FIGS. 2, 4 and 5. Spacers 100 of the disclosure may be inset into the intervertebral disc space at a collapsed height, and then expand axially (superior/inferior) to restore height loss in the disc space. Spacer 100 provides distraction as well as achieves optimal separation of adjacent vertebrae, or disc height restoration. When inserted in a collapsed state, Spacers 100 have a reduced height profile which reduces adverse impact to tissue adjacent to and within the joint space during insertion, while presenting the least visually blocking or physically obstructing profile. Spacer 100 may be reduced in height after implantation, for example by inserting a tool through a minimal incision, to perform a therapeutic height adjustment. Spacer 100 may also be reduced in height to a compressed configuration, to facilitate removal from the body. Spacer 100 supports the cortical rim of adjacent vertebrae, and distributes forces across the vertebra, thereby maximizing vertebral endplate preservation.

Spacer 100 includes two separable endplates 110, 112. A surface 114 of an endplate 110, 112 can be provided with teeth or other projections 116 which can penetrate body tissue to reduce a likelihood of migration of spacer 100 after implantation. Spacer 100 is further secured with one or more fasteners, such as bone screws 300, which pass through an adapter, such as bone screw socket 118 within spacer 100, and into body tissue of the patient. In the embodiment illustrated in FIGS. 1-5, two sockets 118 for two bone screws are provided, although one or more than two fasteners and fastener adapters, may be provided. Bone screws 300 can be retained in connection with spacer 100 by blocking fasteners 120. Bone screw 300 can be a polyaxial screw, and sockets 118 correspondingly shaped, whereby bone screw 300 may be inserted into body tissue at an optimal angle with respect to spacer 100, whereby optimal purchase may be obtained, or certain body tissue may be avoided.

Endplates 110, 112 are moveably connectable to an actuator 150 operable to change a relative relationship of endplates 110 and 112. Actuator 150 includes a frame 152 rotatably supporting an actuator screw 154, and a moveable carriage 156. As actuator screw 154 rotates within frame 152, carriage 156 slides within frame 152, driven by cooperation between threads 158 upon actuator screw 154, and mating threads 160 within frame 152. An implantation tool engagement surface 330 may be provided upon or within spacer 100, configured to receive a tool to enable secure manipulation of spacer 100 during implantation or removal from the body.

In the embodiment of FIGS. 1-6, endplates 110 and 112 are formed in two connected portions, including a portion 122, 122A which can be polymeric, for example PEEK, and a fixation portion 124, 124A, which can be metallic, for example titanium, although other materials may be used. For example, material used for fixation portion 124 should withstand the bending forces exerted by a fastener, for example bone screw 300, passing therethrough. In contrast, endplate material advantageously resiliently withstands a pressure applied by weight of the body. In this regard, both materials could also be polymeric, for example, but of different types of polymer.

The portions 122, 124 or 122A and 124A are joined in the embodiment shown by screws, a mechanical interlock, adhesive, or other fasteners, possibly in combination, as explained further herein. Metallic portions 124, 124A can provide greater strength for portions of spacer 100 which are under relatively greater stress, for example portions through which a fastener may pass to anchor spacer 100 within the body. While portions 122, 122A, 124, 124A are described as polymeric or metallic, it should be understood that other materials may be used, and that the portions can be of similar or dissimilar materials, as described further herein.

Figure 2:
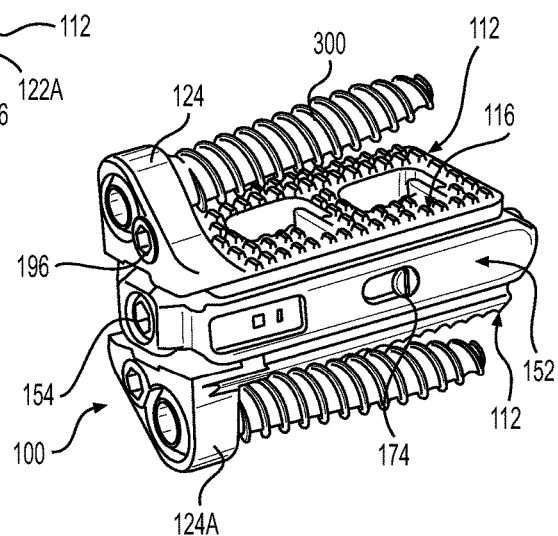
FIG. 2 depicts the spacer of FIG. 1, in an increased height, or expanded configuration.
Figure 3:
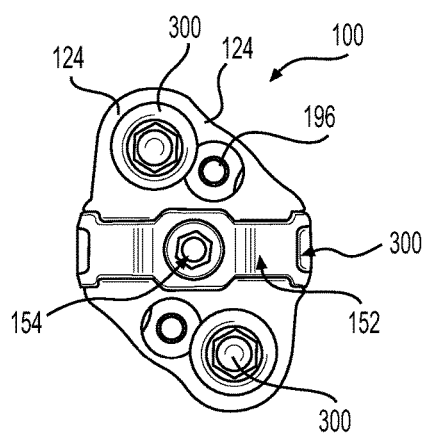
FIG. 3 depicts a front view of the spacer of FIG. 1.
Figure 4:
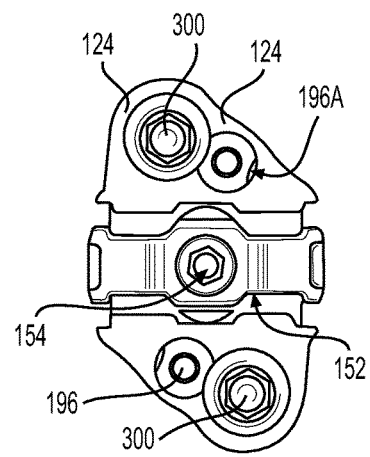
FIG. 4 depicts a front view of the spacer of FIG. 2.

With reference to FIGS. 1 and 3, it may be seen that spacer 100 is in a compressed state, having a lower height relative to an expanded state, as shown in FIGS. 2 and 4. A functioning of device 100 may be best understood with reference to FIG. 5, which is a cross-section through the center of spacer 100. Endplates 110 and 112 are provided with ramps 164, sized to slidingly receive ramps 168 disposed upon carriage 156. While three mating ramps 164, 168 are illustrated for each endplate 110, 112, it should be understood that one, two, or more than three sets of ramps 164, 168 may be provided. Mating ramps 164, 168 operate to enable a reduction or increase in height by sliding against each other as actuator screw 154 is rotated. Interlocking flanges 204, 204A rotatably couple actuator screw 154 and carriage 156, whereby actuator screw may rotate and advance or retard in connection with frame 152, concomitantly advancing or retarding carriage 156 along a longitudinal axis of spacer 100 extending from a distal end 186 and a proximal end 182 of frame 152. A reduction in height is further fostered by a pressure exerted by body tissue.

Figure 5:
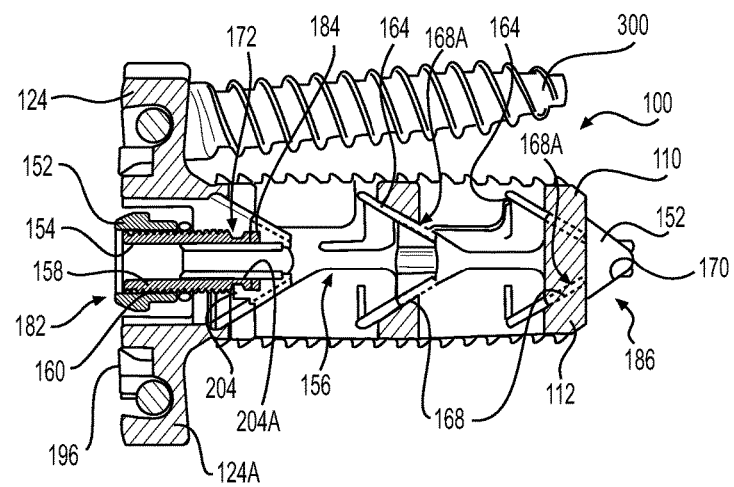
FIG. 5 depicts a cross-section taken through a center of the spacer of FIG. 2.

As may further be seen in FIG. 5, ramps 164 can include channels 164A within endplates 110, 112, and ramps 168 may include dovetail portions 168A which extend into ramps 164. By projecting a dovetail portion 168A of ramp 168 into channels 164A, endplates are moveably affixed to carriage 156. Dovetail portions 168A and channels 164A may further support a predetermined relative orientation of endplates 110, 112 when in a compressed or expanded configuration, while they are being expanded, and when spacer 100 is inserted and removed from the body. It should further be understood that a relative orientation of endplates 110, 112 may be substantially parallel, or may be non-parallel, for example to produce an effective lordosis. Further, planes defined by an interior portion of endplates 110, 112 may be relatively parallel, but bone contacting surfaces may be relatively non-parallel.

Carriage 156 is alternatively or further supported by frame 152 by lateral engagement means, in the embodiment shown there are two support screws 174 engaged with carriage 156, and passable through respective channels 176 formed in frame 152.

A hex driver (not shown) is inserted into engagement with an end of actuator screw 154 at a proximal end 182 of frame 152. As actuator screw 154 is turned, distal end 172 bears against a thrust washer 184, and an end portion of frame 152. As actuator screw 154 rotates in one direction, carriage 156 is driven along actuator screw by interaction of threads 158 and 160 and flanges 204, 204A. As carriage 156 moves, endplates 110, 112 are urged to move along ramps 168, and 168A if present, causing endplates 110, 112 to thereby moving relatively apart, and to increase a height of spacer 100. Endplates 110, 112 are moved relative to carriage 156 by abutting against an end portion 186 of frame 152. End portion 186 can include an internal ramped surface 170 mateable with a ramp 168, as shown in this embodiment, thereby providing additional stability in an expanded configuration.

In a given orientation, one of endplate 110 and 112 is an upper endplate with respect to an orientation in a standing patient. However, spacer 100 may, in some embodiments, be implantable in either of opposite orientations, and therefore designations of upper and lower are provided for ease of understanding, only. It should further be understood that only one of endplate 110, 112 may be moveable with respect to the other. For example, in one embodiment, ramps 168, 168A may not be provided, and endplate 112 may be attached to frame 152.

Figure 7:
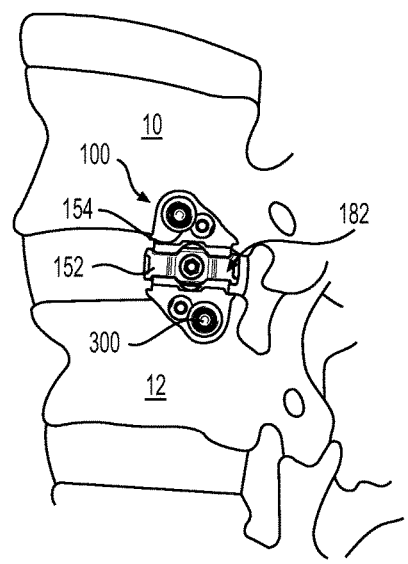
FIG. 7 is a diagram of a possible implantation location in the body, for the spacer of FIG. 1.
Figure 8:
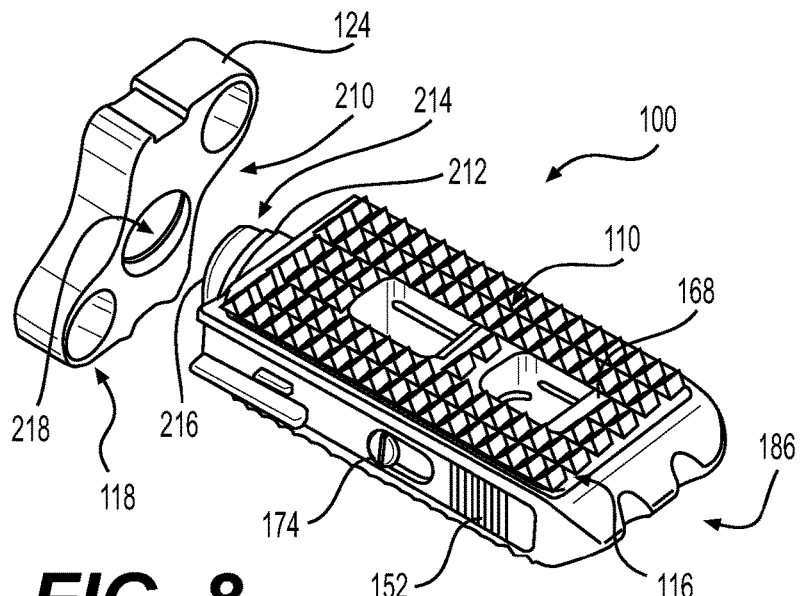
FIG. 8 depicts an embodiment of a spacer in accordance with the disclosure, including a fixation plate that is removeably connectable to a remainder of the spacer, the fixation plate shown removed.
Figure 9:
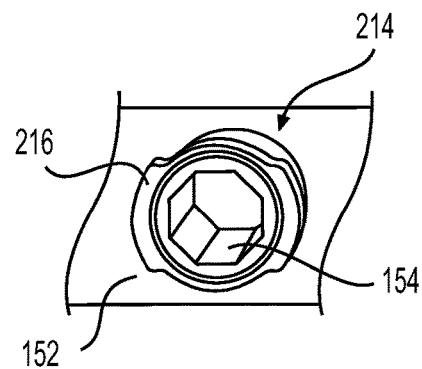
FIG. 9 depicts a connector for connecting the fixation plate to a remainder of the spacer, with respect to FIG. 8.
Figure 10:
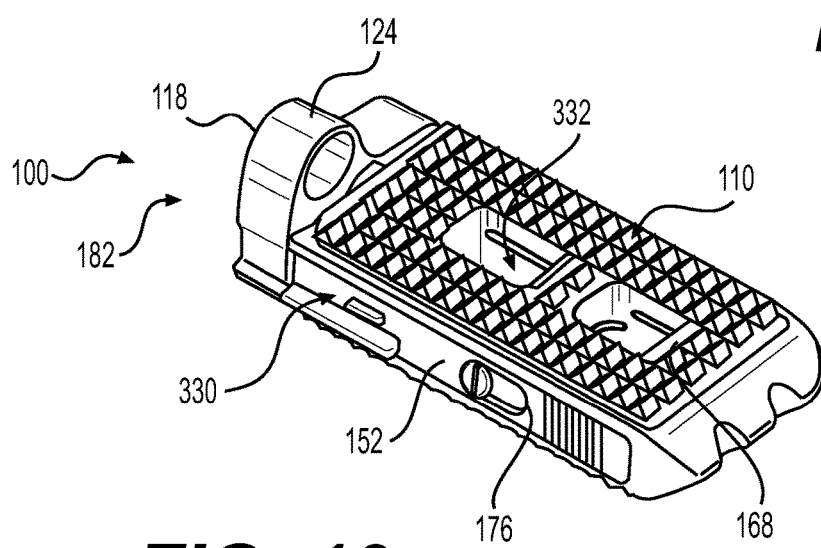
FIG. 10 depicts the spacer of FIG. 8, the fixation plate attached.

FIG. 7 illustrates a spacer 100 of the disclosure implanted between adjacent vertebrae 10, 12. Frame 152 defines a distal or leading end 186 which is inserted first into the body, and a proximal or trailing end 182 which passes last into the body, the distal and proximal ends defining a longitudinal axis extending therebetween. Spacer 100 can be inserted into the body, and into a position between vertebrae, using minimally invasive methods, for example using a small incision, and spacer 100 may be passed through a cannula or other structure which maintains a pathway through body tissue. Spacer 100 may be inserted into the spinal column through any approach, including anterior, anterolateral, lateral, posterolateral, or posterior. A portion of the disc annulus, and nucleus pulposus may be removed in order to form a space into which spacer 100 may be inserted.

Spacer 100 can be inserted when configured to have a lower height profile, as shown in FIGS. 1 and 3, whereby an extent of distraction of body tissue may be reduced during insertion. Moreover, to the extent that spacer 100 is used to open a pathway towards an implantation site, trauma to adjacent tissue is reduced relative to inserting a spacer having a final height profile. Once spacer 100 is positioned between adjacent vertebrae, actuator screw is rotated by a tool. The tool may be positioned entirely within the body, or can extend from in interior of the body to outside the body, for example having a driving tip at one end and having a handle at an opposite end, with a shaft extending into the body between each end.

Once actuator screw 154 has been rotated to separate endplates 110, 112 a desired amount, the tool is removed. At this point, actuator screw 154 may be secured in place, for example using a mechanical block, or an adhesive, to prevent unintended rotation of actuator screw 154. As carriage 156 is slideably moved by rotation of actuator screw 154, ramps 164, 168 of endplates 110, 112 slide against each other, to cause the endplate to move along an axis transverse to the longitudinal axis of the frame, to increase a height of the spacer. Rotation of actuator screw 154 in an opposite direction causes movement along an axis transverse to the longitudinal axis of the frame to decrease a height of the spacer.

Figure 6:
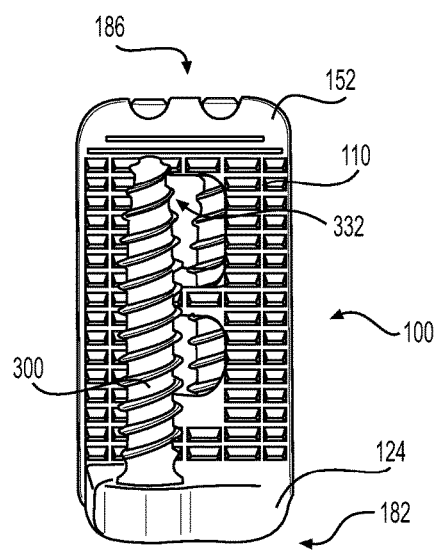
FIG. 6 depicts a top view of the spacer of FIG. 1.

In FIG. 6, it may be seen that spacer 100 has an elongated, narrow profile, facilitating insertion from a lateral approach. Bone ingrowth apertures 332 may be provided, to promote the ingrowth of bone of the patient to further stabilize spacer 100, or to achieve fusion, should that be a therapeutic objective.

Polymeric insets, or a polymeric square nut, for example PEEK, can be provided, engageable with threads 158 or other portion of actuator screw 154, to provide additional friction to prevent height loss under load, particularly under cyclic loading. Similarly, once bone screws 300 have been inserted, blocking elements 196 may be rotated to extend over an end of bone screw head 302, preventing screw 300 from backing out. To enable insertion of bone screw 300, a notched portion 196A is formed in blocking element, and which may be rotated into a position adjacent aperture 118. A similar mechanical block (not shown) may be provided for actuator screw 154.

With reference to the figures, it may be seen that sockets 118 move with endplate 110 or 112, as spacer 100 expands to a final height, whereby sockets 118 overlie cortical bone of vertebrae 10, 12 after spacer 100 is expanded.

In an embodiment, spacer 100 of the disclosure provides an actuator that translates relative to the body by means of a threaded actuator screw 154. Ramps 168, 168A on a carrier 152 mate with ramps 164, 164A on endplates 110, 112. Linear translation of carriage 152 causes endplates 110, 112 to expand spacer 100 along an S/I axis with respect to the body.

In one embodiment, two bone screws 300 are used to provide fixation into adjacent vertebral bodies, a screw extended from each of endplates 110 and 112. Spacer 100 can thus be narrow, to therapeutically fit between vertebrae when inserted from a lateral approach. However, one screw, or more than two screws 300 may be used. Bone screws 300 can have spherical or otherwise curved heads, facilitating insertion at a desired angle, or may be provided to mate with socket 118 in a fixed orientation, for example depending on a diameter of a neck portion of screw 300. Cam type blocking fasteners 196 can be used to block bone screws 300 from backing out after being inserted.

Referring now to FIGS. 8-12, a spacer 100A is similar to spacer 100, however a fixation plate 210 is rotatably fastened to a collar 212 extending from frame 152A. The collar includes an interlock 214, in the example shown a twist-lock connector, although any means of mechanically fastening fixation plate 210 to the remainder of spacer 100A may be used, provided that fixation plate 210 and actuation screw 154 may be rotated as described herein. Fixation plate 210 enables spacer 100A to be inserted into the body with fixation plate 210 rotated to have a longitudinal axis aligned with a transverse axis of spacer 100A, whereby the combined spacer 100A and fixation plate 210 may have a reduced height, and whereupon a reduced sized incision may be used to implant spacer 100A with fixation plate attached. After implantation, fixation plate 210 may be rotated, for example about 90 degrees, so that sockets 118 overlie bone of adjacent vertebrae. Rotation may be any amount, however, for example 45 to 135 degrees.

Alternatively, spacer 100A may be implanted without fixation plate 210 attached, and through a reduced size incision, with less disturbance to body tissue. Fixation plate may then be attached to spacer 100A in situ. In this manner, fixation plate 210 may be inserted through the same entry as spacer 100A, with fixation plate 210 aligned along a longitudinal while being passed through the incision. Once positioned proximate spacer 100A, fixation plate 210 may be reoriented to be attached to spacer 100A, and rotated to align sockets 118 with bone. Rotation of fixation plate 210 can be performed after expansion of spacer 100A, facilitating alignment of sockets 118 with bone.

It should be understood that the various embodiments described herein with respect to spacer 100 and frame 152 may be applied equally to spacer 100A and frame 152A, and any other variants thereof described herein, and are described separately only to facilitate an understanding of each embodiment. More particularly, various embodiments of this disclosure are intended to be combinable in a manner that would be apparent to the practitioner and therapeutic for the patient.

In one embodiment, fixation plate 210 may only be attached to spacer 100 when a longitudinal axis of fixation plate 210 is substantially aligned with a transverse axis of spacer 100, and when fixation plate 210 is rotated to overlie bone, fixation plate 210 is securely affixed to spacer 100. For example, in FIG. 9, an embodiment of interlock 214 is illustrated, including flanges 216 which engage mating flanges 218 disposed upon fixation plate 210. Flanges 216, and or the mating flanges, can be ramped or cammed, so that when engaged, fixation plate 210 and spacer 100 become progressively more tightly interconnected.

In another embodiment, shown in FIGS. 13-17, fixation plate 210 is preliminarily held in place using a snap-fit connector 220, functioning to secure fixation plate to spacer 100, or cooperating with interlock 216. Snap-fit connector 220 forms at least a preliminary connection between fixation plate 210 and spacer 100, to facilitate handling by the medical practitioner. A plate mounting screw 334 may be connected, for example threaded into a threaded bore of actuator screw 154, to further secure fixation plate 210 to a remainder of spacer 100. Fixation plate may be rotated when connected by snap-fit connector 220. Set screws 226 may be passed through apertures 226A to affix fixation plate 210 once it has been rotated. Snap fit connector 220 comprises extension tangs 222 extend from spacer 100, and form a resilient interference fit with snap-fit aperture 224 upon fixation plate 210. Snap-fit aperture 224 may be formed upon spacer 100, and extension tangs may extend from fixation plate 210. Additionally, references to spacer 100 should be considered to include similar embodiments, including spacer 100A.

Figure 11:
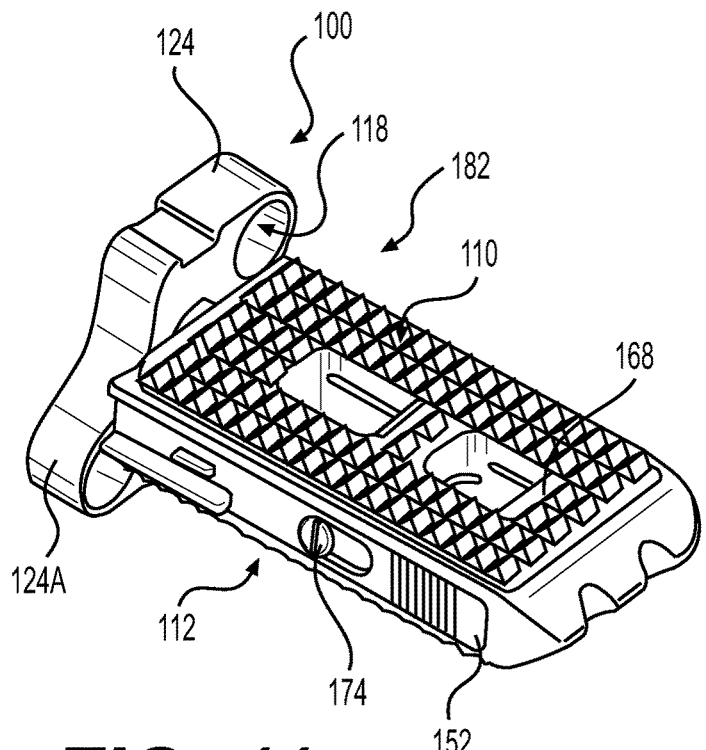
FIG. 11 depicts a reverse side of the spacer of FIG. 10.
Figure 12:
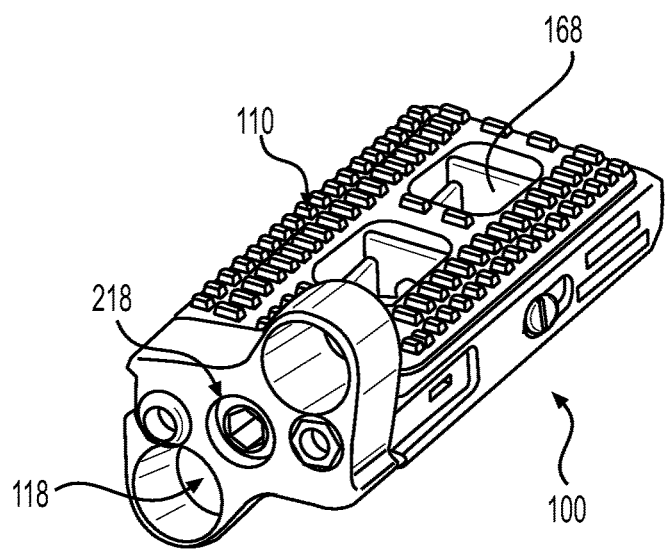
FIG. 12 depicts a front view of the spacer of FIG. 10.
Figure 15:
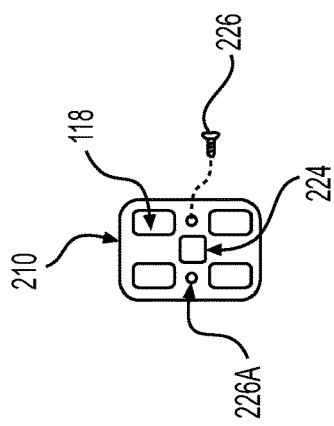
FIG. 15 depicts the fixation plate of FIG. 13.
Figure 14:
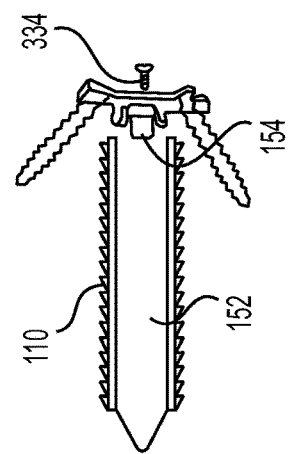
FIG. 14 depicts the spacer of FIG. 13, the fixation plate snap-fit into attachment.
Figure 13:
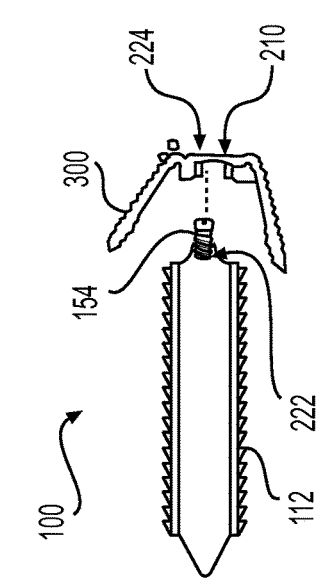
FIG. 13 depicts a side view of an embodiment of a spacer in accordance with the disclosure, the spacer including a detached fixation plate having a snap-fit attachment.
Figure 17:
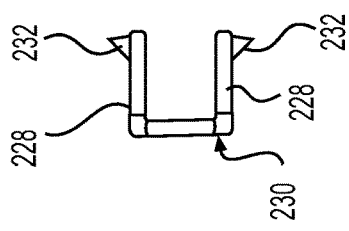
FIG. 17 depicts the hinged fixation plate of FIG. 16, the hinged portions folded, and further showing barbs upon the hinged portion.
Figure 16:
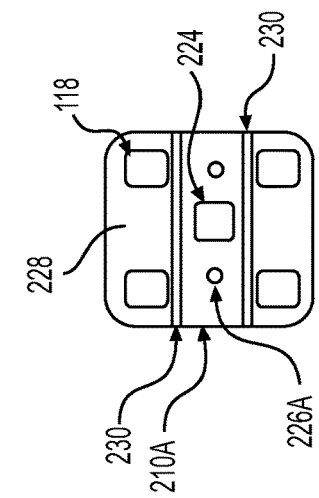
FIG. 16 depicts a hinged fixation plate in accordance with the embodiment of FIG. 13.

With reference to FIGS. 16 and 17, fixation plate 210A includes, in another embodiment of the disclosure, folding or hinged portions 228 which may contain sockets for bone screws 300 or other fastener. When inserting fixation plate 210A, hinged portions 228 are folded either on a lateral, longitudinal, or other axis of the fixation plate along one or more hinges 230, as shown in FIG. 11, to reduce a maximum dimensional profile of fixation plate 210A. In this manner, fixation plate 210A may pass through a reduced size incision as compared to a requirement for an unfolded fixation plate. In an embodiment, tangs or barbs 232 may extend from fixation plate 210 or 210A. to engage body tissue, for example cortical bone of a vertebra, to provide further fixation and stability when bone screws are passed through the fixation plate and into body tissue. Additionally, hinged portions 228 may be angled to permit a bone fastener passed therethrough, for example bone screw 300, to enter bone of the joint at a beneficial or desired angle.

Figure 18:
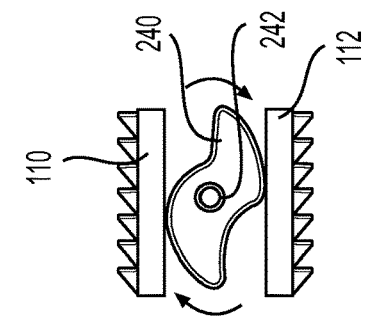
FIG. 18 depicts an embodiment of a spacer in accordance with the disclosure, including cams operative to increase a height of the spacer, the spacer in a reduced height configuration.
Figure 19:
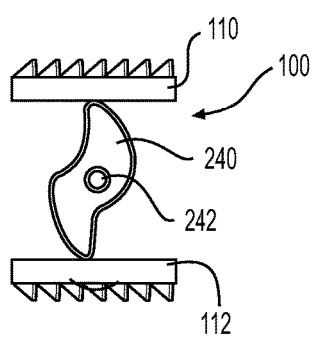
FIG. 19 depicts the spacer of FIG. 18, the cams actuated to increase a height of the spacer.

Referring now to FIGS. 18-19, one or more expansion cams 240 are disposed between endplates 110, 112. A tool is inserted into a socket 242 which may be rotated to rotate the cam (as shown by arrows) to separate endplates 110, 112. Expansion cams 240 can be supported upon a shaft (not shown) connected to frame 152. Endplates 110, 112 can be supported and guided by ramp channels 164A, 168A, as described with respect to FIG. 5.

Figure 20:
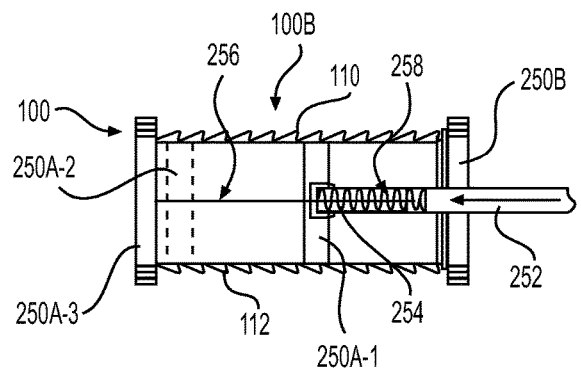
FIG. 20 depicts an embodiment of a spacer in accordance with the disclosure, the spacer including rotatable endplate portions.
Figure 21:
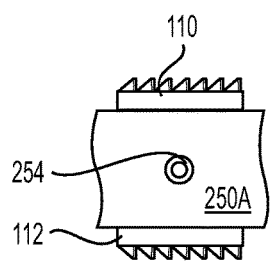
FIG. 21 depicts an end view of the spacer of FIG. 20.
Figure 22:
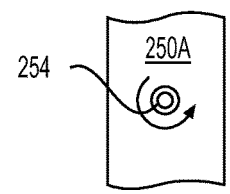
FIG. 22 depicts the spacer of FIG. 21, the rotatable endplate portion rotated.

Turning now to FIGS. 20-22, in an alternative embodiment, endplates 110, 112 include one or more rotating endplate sections 250A, 250B which engage body tissue to therapeutically increase a height of spacer 100B. In the embodiment shown, two rotating endplates sections are illustrated, each containing a transverse dimension having a first width, and a second longitudinal dimension having a second, greater width. Spacer 100B can be inserted into the body with sections 250A, 250B rotated to have a same or lesser height than a remainder of spacer 100B, to reduce an incision size, and to fit within an opening formed between adjacent vertebrae. After spacer 100B has been positioned between vertebrae, sections 250A, 250B may be simultaneously or consecutively rotated to contact body tissue, for example cortical bone, to distract the joint. Section 250B is disposed on a proximal side of spacer 100B, and may be rotated by inserting a tool, for example tool 252, through or into a mating socket 254, and rotating tool 252. Sections 250A, 250B are rotatably coupled to spacer 100B by a pivot shaft, which may be engaged by tool 252, or by another mating engagement between section 250A, 250B and a remainder of spacer 100B, for example a flange (not shown).

Section 250A is inserted first into the body, and to facilitate insertion, and to reduce interference with body tissue, section 250A may be rotated so that section 250A and a remainder of spacer 100B form a compressed or unexpanded profile. For example, section 250A is rotated so that the longest dimension is transverse to an S/I orientation in the body, and is thus adapted to fit within a space formed between adjacent vertebrae prior to distraction. To distract the joint, tool 252 is inserted into an interior of spacer 100B, and is engaged with a socket 254 associated with section 250A, and is rotated to orient section 250A so that a tallest dimension is aligned with an S/I axis of the patient, distracting the joint.

With reference to FIG. 20, in one embodiment, section 250A fits between endplates 110, 112 when rotated in the transverse orientation, to facilitate insertion between vertebrae. After implantation, section 250A is pushed distally to emerge from between endplates 110, 112, whereupon it may be rotated to distract, aid in distraction, or maintain a separation of vertebrae. Tool 252 is connected to section 250A by a tether 256, operative to maintain section 250A in contact with a remainder of spacer 100B, in cooperation with a biasing element 258, disposed within tool 252. In FIG. 20, section 250A is illustrated in three stages of insertion, illustrated by 250A-1, 250A-2, and 250A-3. In the first stage, illustrated as 250A-1, tool 252 is engaged with section 250A and begins pushing section 250A along an interior of spacer 100B defined between endplates 110, 112. In the second stage, illustrated as 250A-2, tool 252 has pushed section 250A to an end of an interior of spacer 100B. In the third stage, illustrated as 250A-3, tool 252 has pushed section 250A to emerge from between endplates 110, 112, whereupon tool 252 may then rotate section 250A to orient a long axis of section 250 along an S/I orientation within the body. Tether 256 may be secured within spacer 100B to maintain section 250A in position at a distal end of spacer 100B. Tool 252 may then be disengaged from spacer 100B and removed from the patient. FIG. 21 illustrates section 250A oriented transverse to an S/I orientation, to reduce a height of spacer 100B. FIG. 22 illustrates section 250A rotated to distract or maintain a separation of vertebra. Projections 260 can be provided, oriented to pierce body tissue to foster maintenance of a position of spacer 100 within the body.

Figure 23:
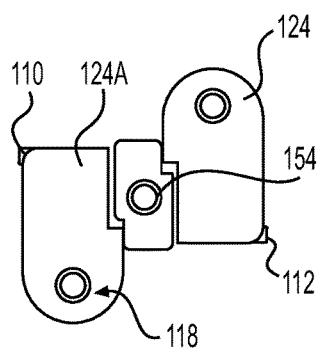
FIG. 23 depicts an embodiment of a spacer in accordance with the disclosure, having endplates that translate together with endplates, as endplates are moved to increase a height of the spacer.
Figure 24:
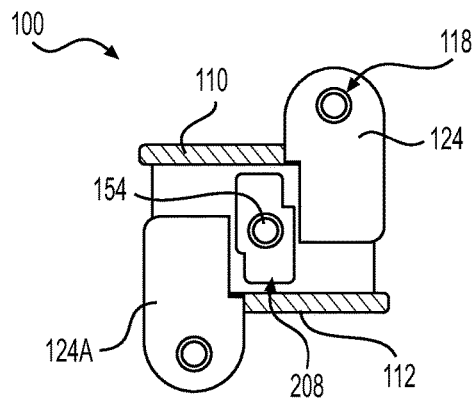
FIG. 24 depicts the spacer of FIG. 23, the spacer expanded to have an increased or expanded height.

Referring now to FIGS. 23-24, fixation portions 124, 124A separate relative to each other as endplates 110, 112 are expanded as described herein. In this embodiment, fixation portions 124, 124A can slideably mate with an actuating section 208, or may only be affixed to their respective endplate 110, 112. One manner of forming a slidable mating connection is described with respect to FIGS. 31-33, herein. By remaining in a fixed position relative to their respective endplate 124, 124A, portions 124, 124A are properly aligned to secure a fastener through socket 118 into cortical bone of adjacent vertebra 10, 12.

Figure 25:
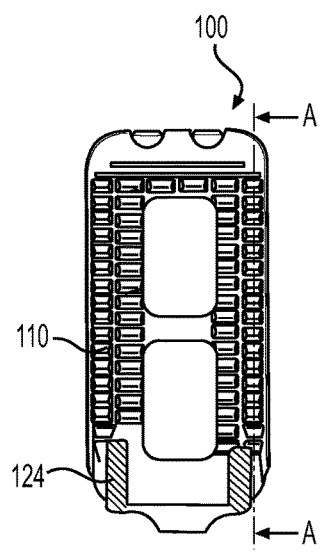
FIG. 25 depicts a side view of an embodiment of a spacer in accordance with the disclosure, the spacer having connectable fixation portions and endplate support portions.
Figure 26:
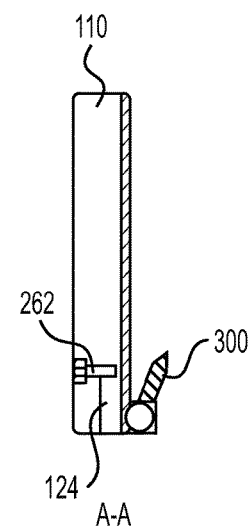
FIG. 26 depicts a cross-section of the spacer of FIG. 25.

In FIGS. 25-26, a manner of connecting endplates 110, 112 to fixation portions 124, 124A is illustrated. Fixation portions 124, 124A and endplates 110, 112 are mutually shaped to be mateably connected, for example by a coupling fastener 262, in this embodiment a screw. In the embodiment shown, endplate 110 and fixation portion 124 are illustrated, however it should be understood that a similar or different connection mechanism may be employed for endplate 112 and fixation portion 124A.

Figure 27:
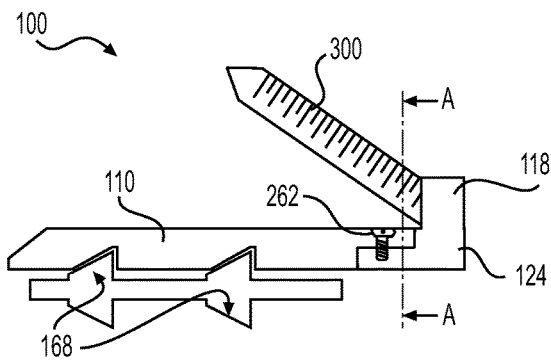
FIG. 27 illustrates an embodiment of a spacer including connectable fixation portions and endplate support portions, the portions connectable by a dovetailed connection.
Figure 28:
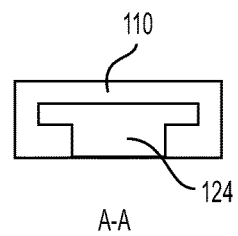
FIG. 28 depicts a cross-section of the device of FIG. 27.

A similar connection between endplate 110 and fixation portion 124 may be seen in FIG. 27, in which it may also be seen that screw 300 can be countersunk within fixation plate 124. Socket 118 may additionally be a polyaxial socket, and can include a blocking element 196. FIG. 28 illustrates that the in addition to, or in an alternative to the use of coupling fastener 262, endplate 110/112 and fixation portion 124/124A may be joined by shaped coupling, for example a dovetail, tounge-in-groove, or T-connection. As an alternative to coupling fastener 262, an adhesive may be used, or alternatively, the shaped coupling may produce an interference fit between endplate 110/112 and fixation portion 124/124A. While FIG. 28 illustrates fixation portion 124 (or 124A) inserted within endplate 110 (or 112), it should be understood that this configuration could be reversed, with endplate 110/112 inserted within fixation portion 124/124A.

Figure 29:
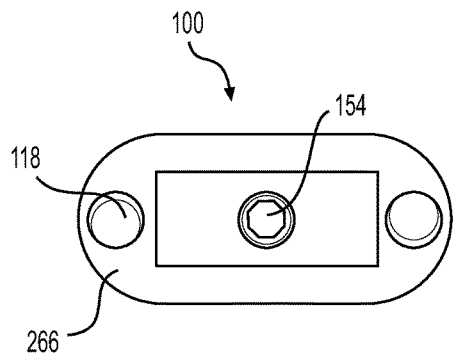
FIG. 29 depicts an embodiment of a spacer of the disclosure, including a rotatable fixation plate.
Figure 30:
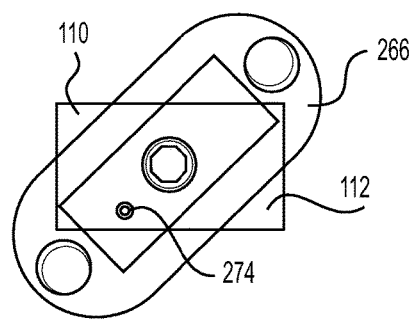
FIG. 30 depicts the spacer of FIG. 29, the fixation plate rotated.
Figure 30A:
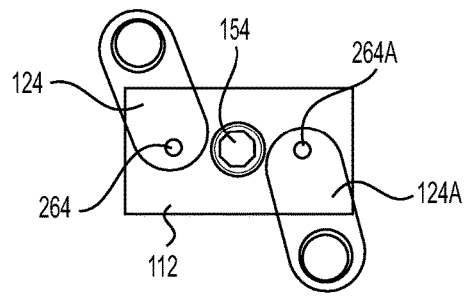
FIG. 30A depicts an embodiment of a spacer of the disclosure, including two rotatable fixation plates, rotated to a deployment position.

In FIGS. 29-30, fixation portions 124, 124A swivel so that socket 118 can be positioned over cortical bone of a vertebra 10, 12. In the illustration, portions 124, 124A are connected, or are formed as a single rotating fixation plate 266, and rotate together about a single pivot. In FIGS. 29-30, the pivot is centrally located about the same axis as actuator screw 154, however the pivot may be located elsewhere. In one embodiment, an endplate pivot pin 274 extends between an endplate 110/112 and plate 266, causing plate 266 to rotate about the central axis as endplate 110/112 is moved with respect to the central axis. Alternatively, as illustrated in FIG. 30A, fixation portions 124, 124A may be separate, and each pivot on its own pivot, 264, 264A. In this embodiment, as well as other pivoting embodiments, one or more endplate pivot pins 274 may be provided to cause a controlled rotation of a rotatable plate, for example one or both of separated plates 124, 124A.

With reference to FIGS. 31-33, rotating fixation plate 268 is formed in two slidingly mateable plates 268A, 268B. An exemplary interconnection between plates 268A, 268B is illustrated in FIG. 33, in which a dovetail or interlocking engagement 270 may be seen. In this embodiment, interlocked plates 268A, 268B are secured in connection with a remainder of spacer 100, and rotate about, a pivot 272. In one embodiment, pivot 272 is associated with actuator screw 154. In a related embodiment, rotation of actuator screw 154 causes a rotation of plate 268 due to a mechanical connection between actuator screw 154 and plate 268. In another embodiment, pivot 272 is formed coaxial with, but separate from actuator screw 154.

Referring now to FIGS. 34-35, blades, spikes, pins, or piercing elements 276 are disposed within piercing guides 278 formed within spacer 100, for example within endplates 110, 112. Only relevant portions of spacer 100 are illustrated in FIGS. 34-35, to clarify this feature of the disclosure. In one form, piercing element 276A passes through a portion of ramp 164, and is pushed by ramp 168 as actuator screw 154 is rotated to engage mating ramps 164, 168. Piercing element emerges through endplate 110 or 112 to pierce body tissue, for example cancellous or cortical bone of adjacent vertebrae 10, 12. In this manner, spacer 100 is further affixed in a therapeutic location within the body. By providing additional fixation in the form of piercing elements 276, spacer 100 is better adapted to function without supplemental support, as a standalone device, without for example other fixation or fusing devices. Additionally, piercing elements herein can provide sufficient fixation so that a fixation portion 124, 124A can optionally be eliminated, and fixation exterior to the intervertebral space may be avoided.

In another embodiment shown in FIGS. 34-35, piercing element 280 is formed as a resilient curved member which is straightened as it is pushed by a portion of carriage 156. During straightening, piercing element 280 elongates to pass through endplate 110, 112 to pierce body tissue.

In FIGS. 36-37, bone screw 300A is formed with gear teeth 282 disposed to lie along a longitudinal axis of the screw, as well as standard bone engaging threads substantially transverse to this longitudinal axis. Actuator screw 154A includes external gear teeth 284 mateable with gear teeth 282 of bone screw 300A, whereby when either bone screw 300A or actuator screw 154A is rotated, endplates 110, 112 separate to increase a height of spacer 100, and bone screw 300A is simultaneously driven into body tissue to therapeutically secure implant 100 to bone.

FIGS. 38-40 illustrate a method of connecting endplate 110/112 to fixation portion 124/124A, using a mortise and tenon or dovetail connection 286. A keyed aperture 288 disposed within fixation portion 124 or endplate 110 mateably receives a correspondingly shaped projection 290 in the other of fixation portion 124 and endplate 110. A similar connection may be formed between fixation portion 124A and endplate 112. Aperture 288 and projection 290 may form an interference fit, or may alternatively be secure in mating conformity using a set screw or adhesive, for example.

With reference to FIG. 41, it may be seen that one or both of endplate 110, 112 may be beveled, truncated, fenestrated, or shaped with a gap, groove, or channel 292 in endplate 110, 112, dimensioned to permit passage of a bone screw 300, whereby a maximum height of spacer 100, with the exception of bone screw 300, is defined by an expanded height of endplates 110, 112. Channel 292 can allow passage of a shank 294, or any other portion of bone screw 300 or other fastener, so that socket 118 does not lie at a height greater than an endplate 110, 112.

Turning now to FIGS. 42-44, an embodiment of the disclosure includes one or more piercing elements 276A, pivotally mounted to rotatable deployers 310. Piercing elements 276A may have any shape which is adapted to pierce, grip, or engage body tissue, including pin, spike, or blade configurations. Although drawn as separate blades in FIG. 42, it should be understood that elements 276A may extend along a substantial length of a longitudinal axis of spacer 100, and may be supported by one, two, or more deployers 310. An axle, pin, or shaft 296 pivotably mounts deployer 310 to frame 152, carriage 156, or other mounting point of suitable strength, upon spacer 100, so that deployers 310 may rotate about a longitudinal axis aligned with a longitudinal axis of spacer 100, although mounting along a different axis can be provided. In FIGS. 42-44, spacer 100 is illustrated without endplates 110, 112 and associated ramps, to simplify the illustrations. It may be seen, however, that ramps 164, 168 may be reduced in size to allow room for one or more deployers 310.

In use, a tool (not shown) is engaged with an engagement port 198 and is rotated to rotate a deployer 310, to advance piercing element 276A through an opening or gap in an endplate 110/112. In one embodiment, piercing element 276A is fixed to an end of deployer 310, and enters body tissue at an angle with respect to a plane defined by an endplate 110/112. In the embodiment shown, piercing element is pivotally mounted to deployer 310 at pierce pivot 312, and can be guided, for example by guide 314, which may be a shaped channel in endplate 110/112, to enter body tissue, for example bone of a vertebra 10/12, substantially perpendicular to a plane defined by an endplate 110/112, or at a particular desired angle or within a range of angles. Piercing elements 276A therapeutically secure implant 100 to bone or body tissue of the joint.

FIGS. 45-47 contain elements analogous to FIGS. 42-44, however deployer 310 rotates about a common axis with actuator screw 154, and therefore relatively larger ramps 164, 168 can be maintained. Piercing elements 276B may further be longer, as a length of an arm 316 of deployer 310A may be longer.

In FIG. 48, a collar 320 is connected to deployer 310A, and rotates about a common axis with actuator screw 154, but may be rotated independently of actuator screw 154 using tool engagement port 322. In another embodiment, actuator screw is directly connected to deployer 310A, and causes deployment of piercing elements 276A as endplates 110, 112 are expanded as described herein. In a yet further embodiment, actuator screw rotates deployer 310A through a gear reduction (not shown), whereby deployer 310A rotates about the common axis more slowly than actuator screw 154, so that increased leverage may be applied to piercing elements 276A.

With reference to FIG. 49, in an embodiment of the disclosure, endplates 110, 112 can pivot about an axis 324 extending transverse to a longitudinal axis of spacer 100, or along an axis that extends along an S/I direction when spacer 100 is implanted within a patient. For example, one or more pivot pins 326 may extend from an endplate 110 to frame 152, or may extend from endplate 110 to endplate 112. In this manner, spacer 100 may accommodate an additional rotational degree of freedom, for example, spacer 100 may support six degrees of freedom of movement of adjacent vertebrae. This is accomplished in one embodiment by enabling movement of ramped surfaces 164, 168 with respect to each other, thereby enabling roll, pitch, and yaw of endplate 110/112 with respect to frame 152. While rotation about this axis is explicitly supported in this embodiment, it should be understood that all embodiments herein can be configured to support rotation about axis 324, as well. A rotating fixation plate, for example fixation plate 266, can be provided in this embodiment, as with other embodiments of the disclosure.

Implants of the disclosure enable a continuous expansion and retraction over a range of displacements according to predetermined dimensions of a specific spacer 100 design. This provides the ability to distract vertebral bodies to a desired height, but also to collapse the spacer 100 for repositioning, if therapeutically advantageous for the patient. Endplates 110, 112 may be shaped to form planes or surfaces which converge relative to each, to provide for proper lordosis, coronal correction, or kyphosis and can be provided with openings through which bone may grow, and into which bone graft material may be placed. Spacer 100 may be used to distract, or force bones of a joint apart, or may be used to maintain a separation of bones created by other means, for example retractor. Endplates 110, 112 may additionally be curved to conform to the surface of body tissue, for example the surface of cortical bone, of the vertebra to be contacted, for improved fixation and load bearing.

Spacer 100 may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

For example, metallic portions 124, 124A of endplates 110, 112 may be manufactured from Titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Polymeric portions 122, 122A may be manufactured from ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of spacer 100. For example, polymeric portions 122, 122A can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates 110, 112, to provide for a natural lordosis, or a corrective lordosis, for example of from 0° to 6° for a cervical application, although much different values may be advantageous for other joints. Lordotic angles may also be formed by shaping one or both of plates 110, 112 to have relatively non-coplanar surfaces. Expanded implant heights, for use in the vertebrae for example, may typically range from 3 mm to 25 mm, but may be larger or smaller, including as small as 2 mm, and as large as 30 mm, although the size is dependent on the patient, and the joint into which an implant of the invention is to be implanted. Spacers 100 may be implanted within any level of the spine, and may also be implanted in other joints of the body, including joints of the hand, wrist, elbow, shoulder, hip, knee, ankle, or foot.

In accordance with the invention, a single spacer 100 may be used, to provide stabilization for a weakened joint or joint portion. Alternatively, two, three, or more Spacers 100 may be used, at a single joint level, or in multiple joints. Moreover, Spacers 100 may be combined with other stabilizing means.

Additionally, spacer 100 may be fabricated using material that biodegrades in the body during a therapeutically advantageous time interval, for example after sufficient bone ingrowth has taken place. Further, spacer 100 is advantageously provided with smooth and or rounded exterior surfaces, which reduce a potential for deleterious mechanical effects on neighboring tissues.

Any surface or component of the invention may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, spacer 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 2 at the involved level. The surgery position spacer 100 may be performed through an Anterior, Anterolateral, Posterolateral, Lateral, and/or posterior approach.

In a typical embodiment, spacer 100 has a uncompressed height, before insertion, of 2 to 25 mm, and may advantageously be provided in cross-sections of 23×32 mm, 26×38 mm and 26×42 mm, with 4, 8, 12, or 16 degree lordotic angles, although these are only representative sizes, and substantially smaller or larger sizes can be therapeutically beneficial. In one embodiment a spacer 100 in accordance with the instant disclosure is sized to be inserted using an MIS approach (a reduced incision size, with fewer and shorter cuts through body tissue).

Spacer 100 may advantageously be used in combination with other known or hereinafter developed forms of stabilization or fixation, including for example rods and plates.

Figure 50:
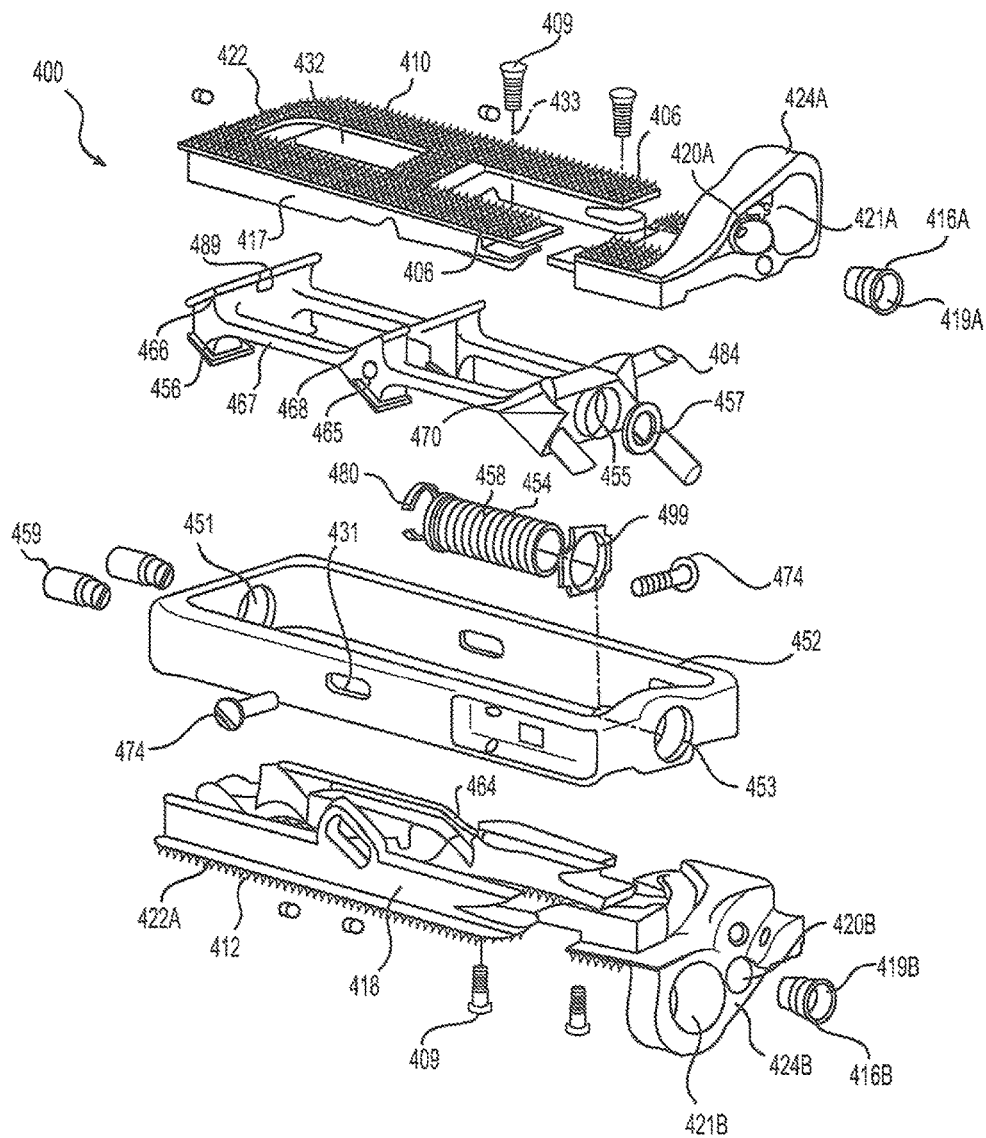
FIG. 50 illustrates an exploded view of an alternative spacer according to some embodiments.

FIG. 50 illustrates an exploded view of an alternative spacer device according to some embodiments. The device 400 comprises a number of components similar to the device 100 described above, including a spacer portion 422 and a fixation portion or plate portion 424. The spacer portion 422 comprises a frame or body 452 for receiving a carriage or translation member 456 therein, an upper endplate 410, a lower endplate 412, and an actuator screw or member 454 for moving the translation member 456 to expand or contract the distance of separation between the endplates. The spacer portion 422 is operably attached to at least one plate portion 424 comprising a bone screw opening 421 for receiving a bone screw (not shown) for insertion into a bone member and a blocking screw opening 420 for receiving a blocking screw 419. With the combined spacer portion 422 and plate portion 424, the device 400 can advantageously serve as a standalone spacer that can be inserted through a number of approaches, including laterally, posteriorly or anteriorly.

In addition to the features described above, device 400 also includes a number of unique features designed to provide a number of different advantages. Among the novel features include: screws 409 designed to secure the spacer portion 422 to the plate portion 424 for enhanced connection; wrap-around portions 417, 418 extending from the upper and lower endplates 410, 412 for enhanced connection; rod extensions 484 extending from the body of the translation member 456 that penetrate into the plate portion 424 for increasing the strength of the device 400 in tension; mating slots 489 (e.g., T-slots or dovetail slots) formed in the translation member 456 for receiving a complementary mating feature in an upper or lower endplate 410, 412 for improved integration; the addition of a c-clip or spring clip 480 to the actuation member 454 to securely hold the actuation member 454 in position relative to the translation member 456; the addition of a PEEK washer 457 in between the interface of the translation member 456 and actuation member 454 to prevent metal-on-metal contact; and a device design with an open center that provides for back fill with bone graft, whether the device is in a compressed or expanded state. These features will be discussed in more detail below.

As shown in FIG. 50, the spacer device 400 is comprised of a spacer portion 422 including a body 452, translation member 456, upper endplate 410, lower endplate 412 and actuation member 454. The spacer portion 422 is attachable to one or more plate portions 424, including one or more bone screw openings 421, blocking screw openings 420 and rod receiving bores 423. In the present embodiment, the spacer portion 422 is attachable to an upper plate portion 424A and a lower plate portion 424B. In some embodiments, while the spacer portion 422 is insertable into a vertebral space between vertebral bodies, the plate portions 424A, 424B are capable of receiving bone screws that penetrate bone to make the device 400 a standalone spacer device.

Further details regarding the spacer portion 422 will be discussed herein. The spacer portion 422 comprises a frame or body 452 for receiving a translation member 456 therein. The body 452 includes a pair of sidewalls separating a front portion and a rear portion. As shown in FIG. 50, each of the sidewalls includes a side slot 431 for receiving a support screw 474 therein. Each of the support screws 474 is configured to extend into a support screw opening 465 formed in the translation member 456, thereby attaching the body 452 to the translation member 456. The front portion of the body 452 includes a pair of openings 451 for receiving one or more stabilizers 459 therein. Advantageously, the stabilizers 459 are configured to help stabilize the translation member 456 in the central opening of the body 452. The rear portion of the body 452 includes an opening 453 for receiving an actuation member (e.g., screw) 454 for moving the translation member 456. Advantageously, the opening 453 can serve as a backfill opening whereby bone graft material or other material is received through the opening 453, regardless of whether the device 400 is in an expanded or contracted state. While in the present embodiment the opening 453 remains open, even after implantation, in other embodiments, the opening 453 can be closed off.

The translation member 456, which is received in the body 452, includes one or more ramps for engaging with ramps on corresponding endplates. As the translation member 456 moves or translates laterally, ramps on the translation member 456 engage corresponding ramps on endplates, thereby causing expansion and/or contraction of the device. As shown in FIG. 50, in some embodiments, the translation member 456 includes three pairs of ramps 466, 468, 470 extending upwardly from the body of the translation member 456, as well as three pairs of ramps extending downwardly from the body of the translation member 456. Ramp 466 is separated from ramp 468 by a first bridge member 467, while ramp 468 is separated from ramp 470 by a second bridge member 467. As the translation member 456 moves laterally, the three pairs of upwardly extending ramps on the translation member 456 engage and interact with downwardly facing ramps of the upper endplate 410, while the three pairs of downwardly extending ramps engage and interact with upwardly facing ramps of the lower endplate 412, thereby causing expansion or contraction of the device. Advantageously, the three pairs of ramps are located along the periphery of the upper and lower surfaces of the translation member 456, thereby leaving a central area of the translation member 456 completely exposed and capable of receiving bone graft or other material therein. While the present embodiment includes the translation member 456 as having three pairs of ramps on an upper surface and a lower surface of the translation member, in other embodiments, the translation member can have one, two or four or more pairs of ramps on either the upper surface or lower surface of the translation member.

The front portion of the translation member 456 includes one or more mating slots 489 (best shown in FIG. 51) on upper and lower surfaces of the translation member 456 for receiving corresponding mating features on the upper and lower endplates 410, 412. In some embodiments, the mating slots 489 comprise T-slots or dovetail slots. These mating slots 489 advantageously hold the endplates 410, 412 on the translation member 456, thereby improving the connection between the translation member 456 and the endplates 410, 412.

The rear portion of the translation member 456 includes an opening 455 for receiving a washer 457 and an actuation member 454 therein. In some embodiments, the washer 457 comprises a PEEK washer, and is advantageously inserted between the interface of the translation member 456 and the actuation member 454, thereby preventing metal-on-metal contact. In addition, the rear portion of the translation member 456 also includes one or more rod extensions 484 (e.g., or bar extensions or other shaped extensions) that extend from a body of the translation member. These novel rod extensions 484 are capable of being received through corresponding rod receiving bores 423 in the plate portions 424. As such, the rod extensions 484 advantageously hold the plate portions 424 such that when the plate portions are in tension, the overall system has greater strength. While in the present embodiment, the translation member 456 includes a pair of upper rod extensions angled upwardly and a pair of lower rod extensions angled downwardly, in other embodiments, the translation member 456 can include a single upper rod extension or lower rod extension, or three or more upper rod extensions or lower rod extensions.

An upper endplate 410 is operably attached to an upper surface of the translation member 456. The upper endplate 410 comprises a textured upper surface having one or more teeth, ridges, ribs, etc. designed to engage an upper vertebral body. Graft windows 432 and 433 are formed through the upper surface of the upper endplate 410, and allow for bone growth material to pass therethrough. As shown in FIG. 50, while graft window 432 is completely enclosed on four-sides by surfaces of the endplate, graft window 433 has an exposed side that is ultimately closed by the plate portion 424. Advantageously, these graft windows 432, 433 are in open communication with the central portion of the translation member 456, which is open and available to receive backfilled graft material or other material therein.

Upper endplate 410 further includes wrap-around portions 417 that extend downwardly from the side sections of the upper endplate 410. These wrap-around portions 417 cover portions of the translation member, thereby advantageously providing a secure interface between the translation member and the endplates, which helps provide strength to the device, particularly when it is placed in tension.

Rear portion of the upper endplate 410 also includes one or more openings 406 for receiving screws 409 therein. The screws 409 are downwardly inserted, and are configured to be inserted through the upper endplate 410 and an upper plate portion 424A to advantageously secure the upper endplate and the upper plate portion together. As shown in FIG. 50, the upper endplate 410 can receive a pair of screws 409. However, in other embodiments, one, three, four or more screws can be received to securely integrate the upper endplate 410 with the upper plate portion 424A.

A lower endplate 412 is operably attached to a lower surface of the translation member 456. The lower endplate 412 shares similar features with the upper endplate 410, including surface texturing, graft windows, wrap-around portions 418, and openings for receiving a pair of screws 409. The screws 409 in the lower endplate 412 are configured to be inserted through the lower endplate 412 and a lower plate portion 424B to advantageously secure the lower endplate 412 and the lower plate portion together.

An actuation member 454 is inserted into the rear opening 455 of the translation member 456 and is operably attached to the translation member 456. The actuation member 454 comprises an actuation screw whereby rotation of the member 454 in one direction causes translation of the translation member 456 in a first direction, thereby causing expansion of the device 400. Reverse rotation of the actuation screw causes translation of the translation member 456 in on opposite direction, thereby causing contraction of the device 400. To secure the actuation member 454 to the translation member 456, the actuation member 454 can be accompanied by a c-clip or spring clip 480 that is attached to a front portion of the actuation member 454. With reference to FIG. 52, as the actuation member 454 is moved laterally, the spring clip 480 can compress under a notch 491 formed in the translation member 456 and can spring into a desired recess 493 formed in the translation member 456, thereby advantageously securing the actuation member 454 to the translation member 456. In some embodiments, the actuation member 454 can include a lock nut or friction nut 499 that forms around the actuation member to stabilize and control the actuation member during rotation.

In the present embodiment, the spacer portion 422 is advantageously connected to an upper plate portion 424A and a lower plate portion 424B. The upper plate portion 424A is configured to receive a screw therethrough to fix the upper plate portion 424A to an upper vertebra, while the lower plate portion 424B is configured to receive a screw therethrough to fix the lower plate portion 424B to a lower vertebra. The upper and lower plate portions are described below.

The upper plate portion 424A comprises an opening 421A for receiving a bone screw therethrough for securing the upper plate portion 424A to an upper vertebra. In addition, the upper plate portion 424A comprises a blocking screw opening 420A for receiving a blocking screw 419A therethrough to prevent inadvertent back-out of the bone screw. In some embodiments, the blocking screw 419A is pre-attached to the upper plate portion 424A prior to inserting a bone screw therethrough. As shown in FIG. 50, the blocking screw 419A can include a cut-away portion 416A. When the cut-away portion 416A is adjacent the bone screw opening 421A, this allows entry of a bone screw therethrough. After the bone screw has been inserted through the bone screw opening 421A, the blocking screw 419A can be rotated to block and prevent the bone screw from inadvertently backing out. In some embodiments, the blocking screw 419A covers an upper surface of an inserted bone screw, while in other embodiments, the blocking screw 419A presses firmly against a side of a head of the bone screw, to thereby prevent backing out of the screw. In addition, the upper plate portion 424A further includes novel rod receiving bores 423A for receiving the rod extensions 484 of the translation member 456, thereby providing a secure connection between the upper plate portion 424A and the translation member 456.

The lower plate portion 424B comprises similar features as the upper plate portion 424A, including an opening 421B for receiving a bone screw therethrough, a blocking screw opening 420B for receiving a blocking screw 419B therethrough, and rod receiving bores 423B for receiving rod extensions 484 of the translation member 456. In some embodiments, both the upper plate portion 424A and the lower plate portion 424B are attached to the upper endplate 410 and lower endplate 412, respectively, via screws 409. In some embodiments, while the spacer device 400 includes both an upper plate portion 424A and a lower plate portion 424B, in other embodiments, the spacer device 400 can include only one of the plate portions.

Figure 51:
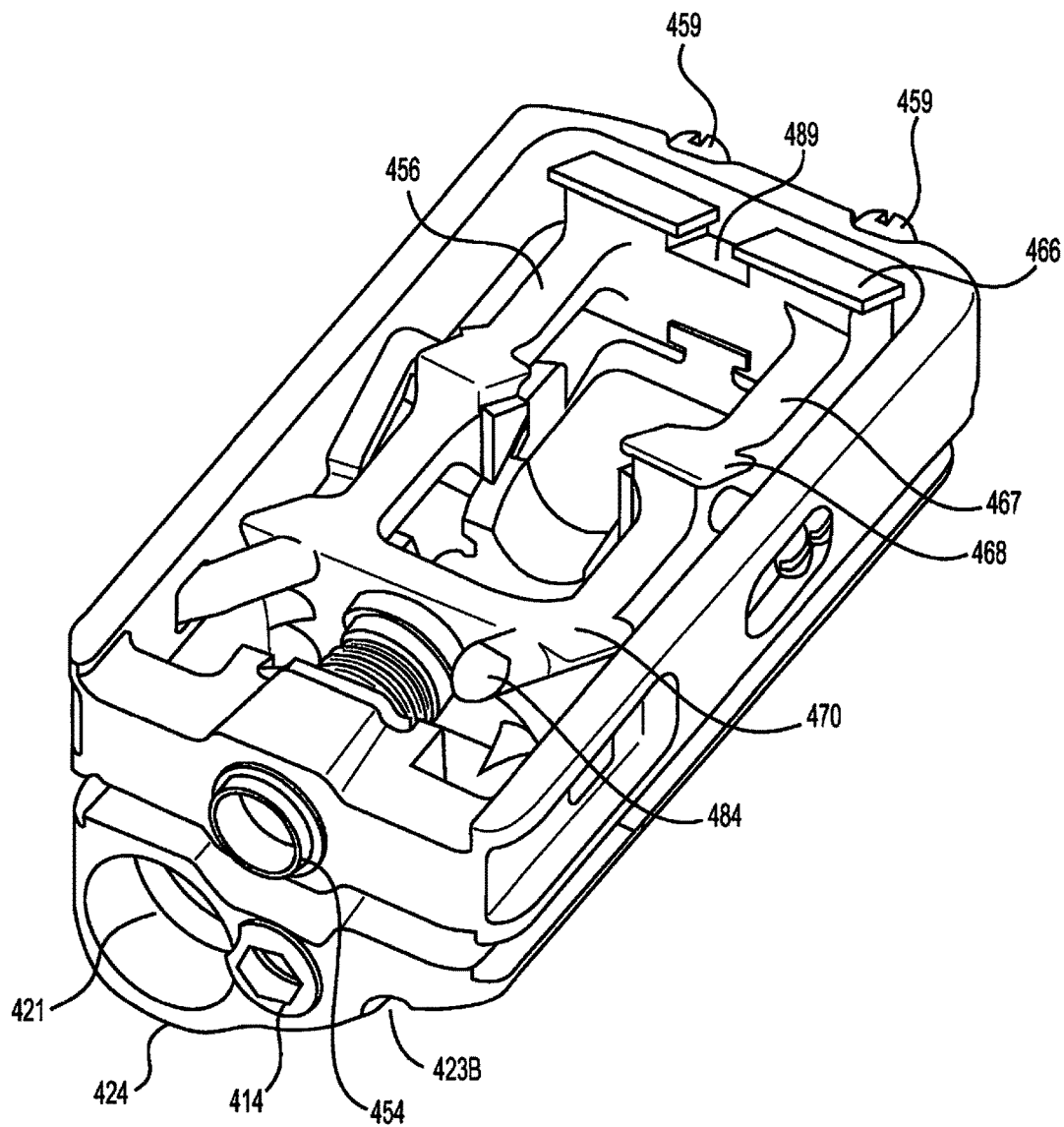
FIG. 51 illustrates a top perspective view of the alternative spacer of FIG. 50 with upper endplate removed.

FIG. 51 illustrates a top perspective view of the alternative spacer of FIG. 50 with upper endplate removed. From this view, one can see how the actuation member 454 is attached to the translation member 456. As the actuation member 454 is rotated in one direction, the translation member can translate laterally in a first direction, thereby causing expansion of the device 400. As the actuation member 454 is rotated in the opposite direction, the translation member can translate laterally in a second direction opposite from the first, thereby causing contraction of an expanded device 400.

From the view in FIG. 51, one can also view the various features of the translation member, including the three pairs of upper ramps 466, 468, 470, the bridges 467 separating the ramps, and the rod extensions 484. In addition, one can view the mating slot 489, which is formed between ramps 466 on a front portion of the translation member.

FIG. 52 illustrates a side cross-sectional view of the alternative spacer of FIG. 50. From this view, one can see how the actuation member 454 is attached to the translation member 456 via the spring clip 480. As shown in the figure, the spring clip 480 of the actuation member 454 is pushed under a notch 491 of the translation member 456, whereby it resides within a recess 493. In addition, from this view, one can see how the device 400, in some embodiments, can include a tapered nose 411 to assist with distraction and insertion of the device 400 into a desired disc space.

FIG. 53 illustrates a different cross-sectional view of the alternative spacer of FIG. 50. In this cross-sectional view, one can see the integration of the support screw 474 within the device 400, which advantageously helps to connect and stabilize the different components.

Figure 54B:
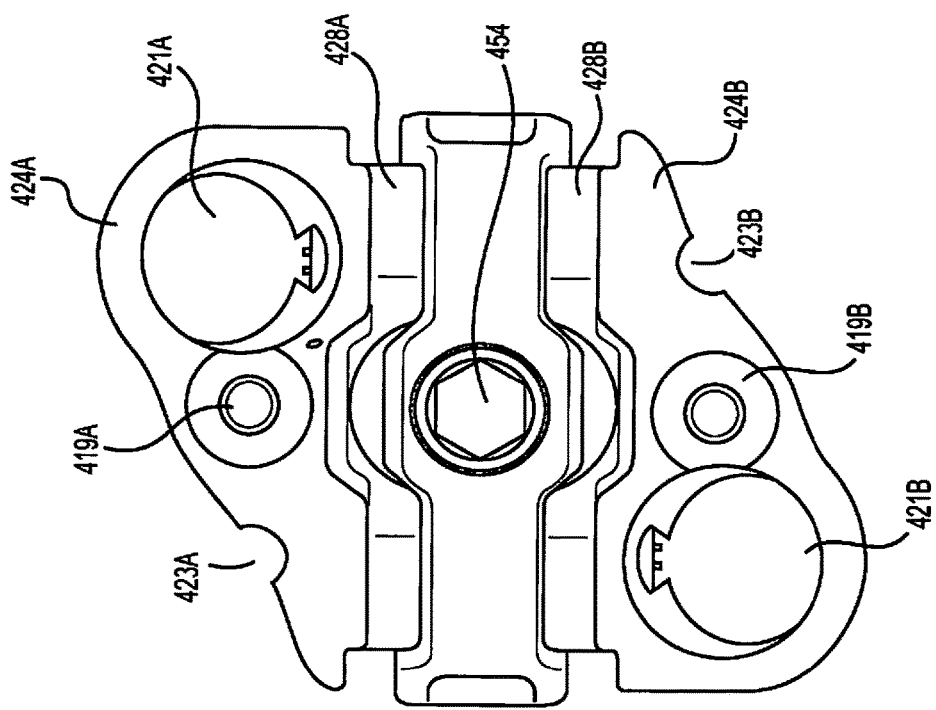
FIGS. 54A and 54B illustrate a rear view of the alternative spacer of FIG. 50.
Figure 54A:
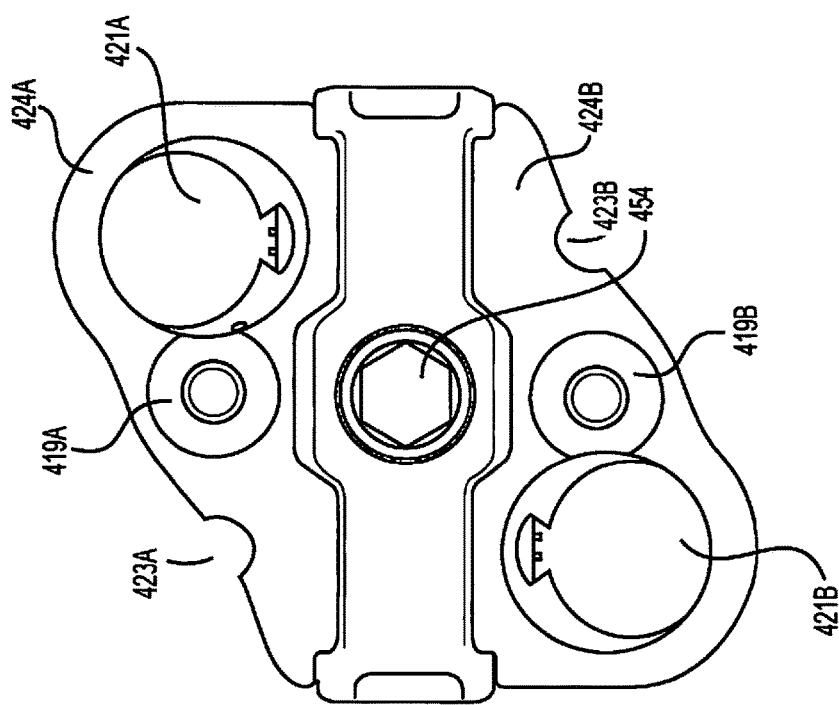

FIGS. 54A and 54B illustrate a rear view of the alternative spacer of FIG. 50. FIG. 54A illustrates the spacer device 400 in a collapsed configuration, while FIG. 54B illustrates the spacer device 400 in an expanded configuration. In some embodiments, as the actuation member 454 is rotated in a first direction, the translation member 456 translates laterally, such that its ramps interact with ramps on corresponding endplates, thereby causing the endplates to separate from one another. This brings the device 400 from a collapsed state to an expanded state. As the upper endplate 410 is attached to an upper plate portion 424A, and the lower endplate 412 is attached to a lower plate portion 424B, movement of the endplates causes movement of the plate portions. When the device is in the expanded configuration, as shown in FIG. 54B, bottom posts 428A of the upper plate portion 424A can be exposed, while top posts 428B of the lower plate portions 424B can be exposed.

Figure 55:
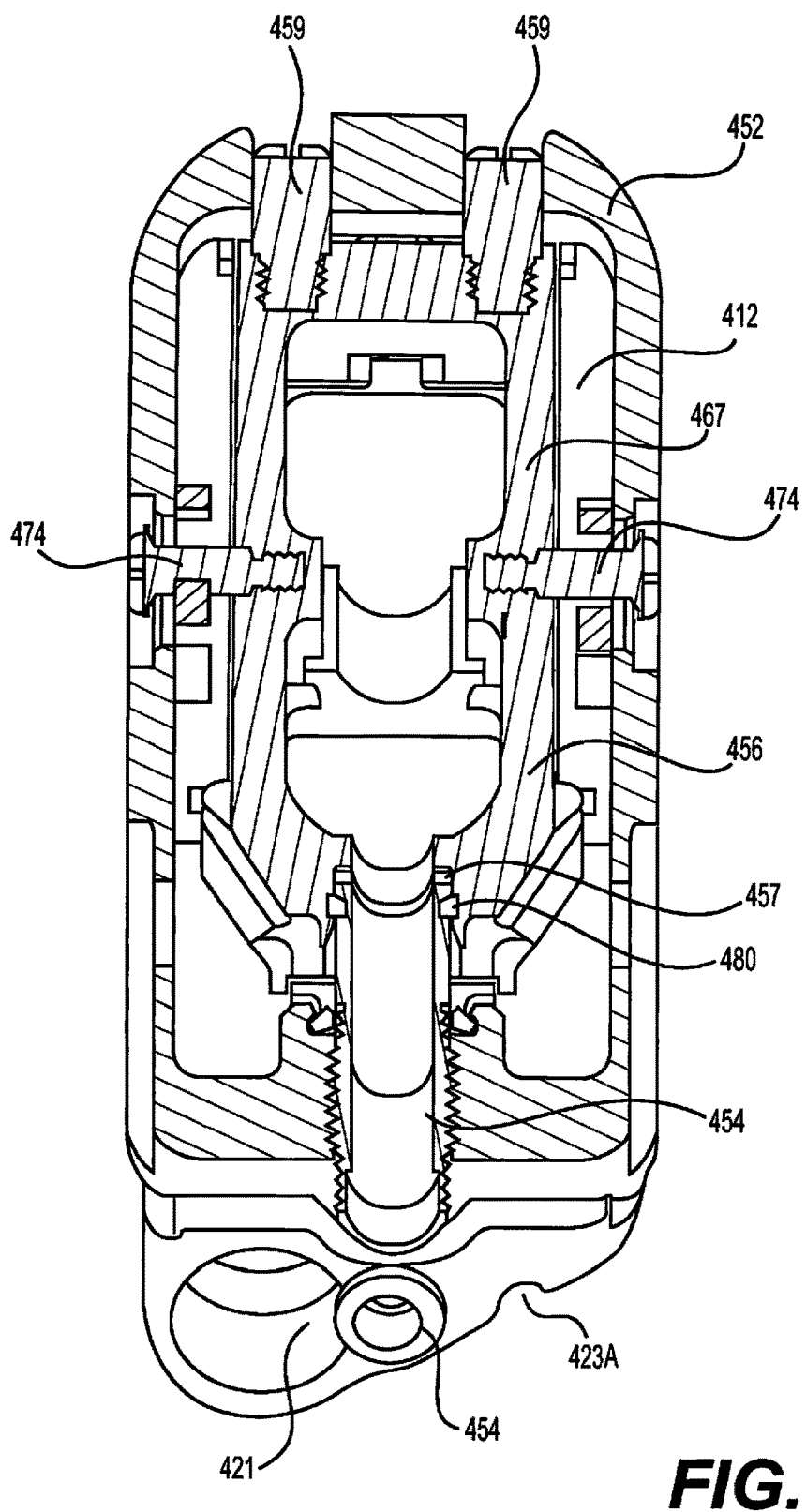
FIG. 55 illustrates a top cross-sectional view of the alternative spacer of FIG. 50.

FIG. 55 illustrates a top cross-sectional view of the alternative spacer of FIG. 50. From this view, one can see how the translation member 456 includes an open central portion, whereby graft material can be filled packed into the device whether it is in a contracted configuration or an expanded configuration. The spacer device 400 provides easy access through the actuation member 454 should one want to provide bone graft or other material into the center of the translation member 456.

Figure 56:
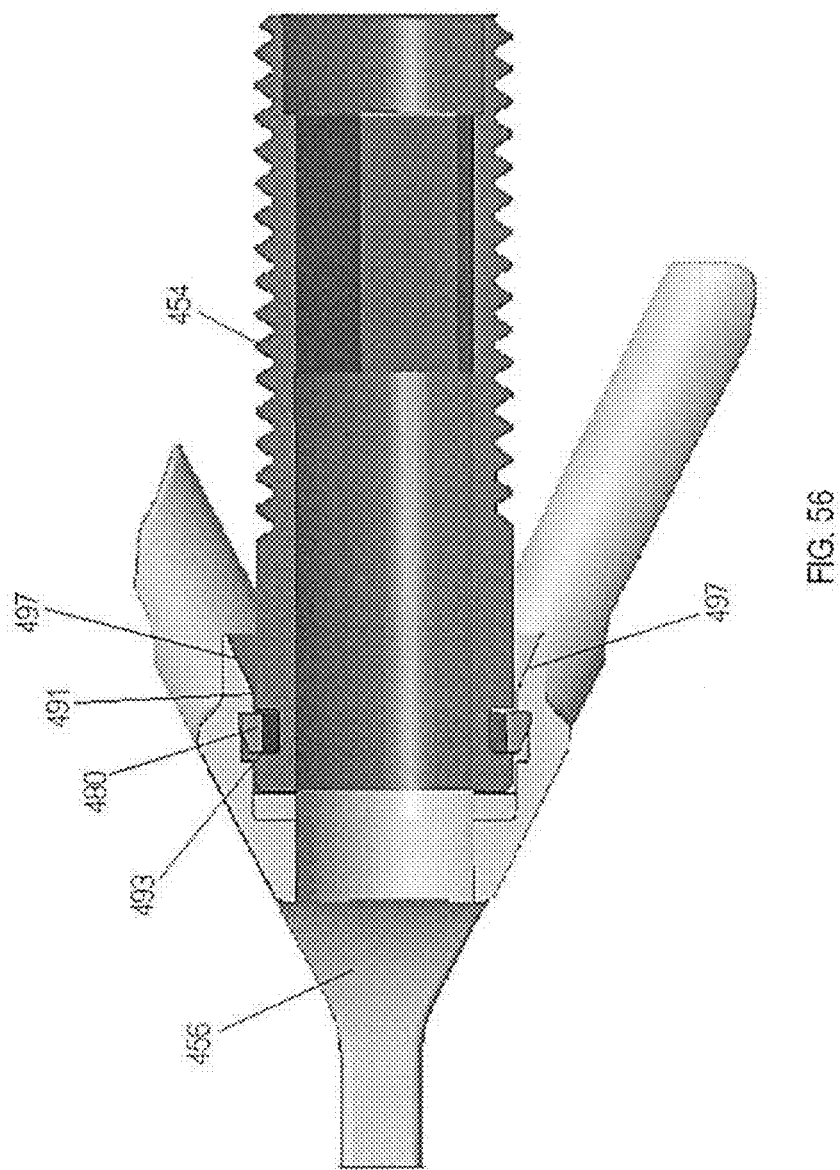
FIG. 56 illustrates a close-up cross-sectional view of the actuation member and translation member of the alternative spacer of FIG. 50.

FIG. 56 illustrates a close-up cross-sectional view of the actuation member and translation member of the alternative spacer of FIG. 50. From this view, one can see how the translation member 456 and the actuation member 454 are joined together. As noted above, a c-spring or clip 480 can be attached to an external surface of the actuation member 454. As the actuation member 454 is forced laterally into the translation member 456, the clip 480 can be forced under a notch 491 in the translation member 456 until it resides in recess 493. From FIG. 56, one can also see how the translation member 456 includes angulated funnel surfaces 497. These funnel surfaces 497 advantageously guide and compress the clip 480 until it is forced under the notch 491.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An orthopedic device comprising:
    a body member including a front portion, a back portion, a pair of opposing sidewalls extending from the front portion to the back portion, and a support screw opening in each of the opposing sidewalls;
    a translation member received in the body member, the translation member including at least one upper ramp portion, at least one lower ramp portion, and a rod extension, wherein the body member is attached to the translation member via a support screw received in the translation member through each of the support screw openings in each of the opposing sidewalls;
    an upper endplate having at least one lower ramp for engaging the upper ramp portion of the translation member;
    a lower endplate having at least one upper ramp for engaging the lower ramp portion of the translation member;
    an actuation member operably connected to the translation member via a spring clip, whereby rotation of the actuation member in a first direction causes the translation member to move in a first direction, thereby causing the distance of separation between the upper endplate and the lower endplate to increase; and
    a friction nut disposed around the actuation member and configured to stabilize the actuation member during rotation of the actuation member,
    wherein the upper endplate is attached to an upper plate portion including an extension and the lower endplate is attached to a lower plate portion including an extension, wherein the upper plate portion comprises an enclosed bore hole for receiving the rod extension of the translation member,
    wherein the upper plate portion includes a through hole for receiving a fastener, and a recess for receiving a fastener back out prevention mechanism, wherein the recess is laterally offset from the through hole of the upper plate portion,
wherein the extension is received in a recess in the upper endplate to couple the upper plate portion to the upper endplate, and
wherein in a contracted position, the upper plate portion and the lower plate portion move toward the body member such that the extensions of the upper and lower plate portions are received in the body member and not exposed, and in an expanded position, the upper plate portion and the lower plate portion move away from the body member such that the extensions of the upper and lower plate portions are exposed.

2. The device of claim 1, wherein the upper endplate is operably attached to the upper plate portion via a pair of screws.

3. The device of claim 2, wherein the screws are positioned perpendicular to the upper endplate.

4. The device of claim 1, wherein the translation member comprises at least three pairs of upper ramp portions.

5. The device of claim 1, wherein the translation member comprises rod extensions extending from a rear portion of the translation member.

6. The device of claim 1, wherein the spring clip is attached to a front portion of the actuation member, and wherein the spring clip is configured to be fit in a recess formed in the translation member.

7. The device of claim 1, wherein the upper endplate and the lower endplate include teeth.

8. The device of claim 1, wherein the upper plate portion is fixed in position relative to the upper endplate, and the lower plate portion is fixed in position relative to the lower endplate.

9. The device of claim 1, wherein an outer surface of the upper plate portion is contoured similarly to an outer shape of the fastener and the fastener back out prevention mechanism.

10. An orthopedic device comprising:
a body member including a front portion, a back portion, a pair of opposing sidewalls extending from the front portion to the back portion, and a support screw opening in each of the opposing sidewalls;
a translation member received in the body member, the translation member including at least one upper ramp portion, at least one lower ramp portion, and a rod extension, wherein the body member is attached to the translation member via a support screw received in the translation member through each of the support screw openings in each of the opposing sidewalls;
an upper endplate having at least one lower ramp for engaging the upper ramp portion of the translation member;
a lower endplate having at least one upper ramp for engaging the lower ramp portion of the translation member;
an actuation member operably connected to the translation member, whereby rotation of the actuation member in a first direction causes the translation member to move in a first direction, thereby causing the distance of separation between the upper endplate and the lower endplate to increase;
a friction nut disposed around the actuation member and configured to stabilize the actuation member during rotation of the actuation member;
an upper plate member including an extension received in a recess in the upper endplate, the upper plate member being attached to the upper endplate via one or more fasteners, wherein the upper plate member comprises an enclosed bore hole for receiving the rod extension of the translation member; and
a lower plate member attached to the lower endplate via one or more fasteners,
wherein the upper plate member includes a through hole for receiving a fastener and a recess for receiving a fastener back out prevention mechanism, wherein the recess is offset from the through hole of the upper plate member,
wherein the lower plate member includes a recess for receiving a fastener back out prevention mechanism, wherein the recess is laterally offset from the through hole of the upper plate member, and
wherein in a contracted position, the upper plate member and the lower plate member move toward the body member such that the extension of the upper plate member is received in the body member and not exposed, and in an expanded position, the upper plate member and the lower plate member move away from the body member such that the extension of the upper plate member is exposed.

11. The device of claim 10, further comprising a PEEK washer positioned at the interface of the actuation member and the translation member.

12. The device of claim 10, wherein the translation member further comprises two or more rod extensions extending therefrom.

13. The device of claim 10, wherein the actuation member is operably connected to the translation member via a spring clip, the spring clip being in the form of a c-ring.

14. The device of claim 10, further comprising a pair of stabilizers positioned in the front portion of the body member.

15. The device of claim 10, wherein the translation member includes at least three pair of ramps on an upper surface of the translation member.

16. An orthopedic device comprising:
a body member including a front portion, a back portion, a pair of opposing sidewalls extending from the front portion to the back portion, and a support screw opening in each of the opposing sidewalls;
a translation member received in the body member, the translation member including at least one upper ramp portion, at least one lower ramp portion, and a rod extension, wherein the body member is attached to the translation member via a support screw received in the translation member through each of the support screw openings in each of the opposing sidewalls;
an upper endplate having at least one lower ramp for engaging the upper ramp portion of the translation member;
a lower endplate having at least one upper ramp for engaging the lower ramp portion of the translation member;
an actuation member operably connected to the translation member, whereby rotation of the actuation member in a first direction causes the translation member to move in a first direction, thereby causing the distance of separation between the upper endplate and the lower endplate to increase;
a friction nut disposed around the actuation member and configured to stabilize the actuation member during rotation of the actuation member;
a washer positioned in between an interface of the actuation member and the translation member;

wherein the upper endplate is attached to an upper plate portion and the lower endplate is attached to a lower plate portion, wherein the upper plate portion comprises an enclosed bore hole for receiving the rod extension of the translation member, and an upper plate portion and a lower plate portion, wherein the lower plate portion includes a through hole for receiving a fastener, an extension, and a recess for receiving a fastener back out prevention mechanism, wherein the recess is laterally offset from the through hole of the lower plate portion, and wherein in a contracted position, the upper plate portion and the lower plate portion move toward the body member such that the extension of the lower plate portion is received in the body member and not exposed, and in an expanded position, the upper plate portion and the lower plate portion move away from the body member such that the extension of the lower plate portion is exposed.

17. The device of claim 16, wherein the washer is a PEEK washer positioned at the interface between the translation member and the actuation member.

18. The device of claim 16, wherein the actuation member comprises a hollow body to allow for bone graft material to be inserted through the actuation member.

19. The device of claim 16, wherein the actuation member is operably connected to the translation member via a spring clip or a c-clip.

20. The device of claim 16, wherein the translation member includes at least two ramp members separated by at least two bridges.

* * * * *